United States Patent [19]

Covey et al.

[11] Patent Number: 5,344,826
[45] Date of Patent: Sep. 6, 1994

[54] TRICYCLE STEROID ANALOGS

[75] Inventors: Douglas F. Covey, Ballwin; Yuefei Hu; Charles F. Zorumski, both of St. Louis, all of Mo.

[73] Assignee: Washington University, St. Louis, Mo.

[21] Appl. No.: 136,150

[22] Filed: Oct. 15, 1993

Related U.S. Application Data

[62] Division of Ser. No. 4,768, Jan. 14, 1993, Pat. No. 5,292,906, which is a division of Ser. No. 811,208, Dec. 20, 1991, Pat. No. 5,206,415.

[51] Int. Cl.$^5$ ............... A01N 45/00; A01N 37/00
[52] U.S. Cl. ................... 514/167; 514/169; 514/562
[58] Field of Search .................. 514/167, 169, 562

[56] References Cited

U.S. PATENT DOCUMENTS

| | | | |
|---|---|---|---|
| 2,830,325 | 4/1958 | Farinacci | 260/168.6 |
| 3,499,913 | 3/1970 | Joly et al. | 260/345.2 |
| 3,676,461 | 7/1972 | Muller et al. | 260/343.3 |
| 3,821,288 | 6/1974 | Crabbe et al. | 260/488 |
| 4,874,891 | 10/1989 | Covey et al. | 560/256 |

FOREIGN PATENT DOCUMENTS

| | | |
|---|---|---|
| 8902272 | 8/1987 | PCT Int'l Appl. |
| 2068363 | 8/1981 | United Kingdom . |

OTHER PUBLICATIONS

Tsushima et al.; Tetrahedron Lett. 23, 1165-8 (1982).
Templeton et al., Can. J. Chem. 56 (15), 2058-64 (1978).
The Merck Index, 11th ed., 1989, No. 6280.
Villotti et al., J. Am. Chem. Soc., 82, 5693-5700 (1960).
Capsi & Balasubrahanyam, Tetrahedron Lett. 12, 745-748 (1963).
Cross et al., J. Med. Chem. 6, 162-166 (1963).
Phillipps et al., in Molecular Mechanisms in General Anesthesia, Eds. Halsey et al., Churchill Livingston, N.Y. 1974, pp. 32-47.
Majewska, Biochem. Pharmacal. 36, 3781-3788 (1987).
Metcalf et al., Tips 10, 491-495 (1989).

*Primary Examiner*—Paul J. Killos
*Attorney, Agent, or Firm*—Scott J. Meyer

[57] ABSTRACT

Novel tricyclic steriod analogs are disclosed which are 1H-benz[e]indene dodecahydro compounds that are useful for enhancing GABA-induced chloride currents at the GABA receptor/chloride ionophore complex and can be represented by the following structural formulas:

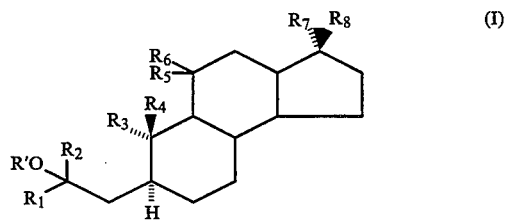

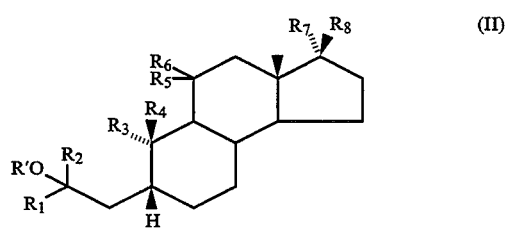

wherein
 $R_1$ = H or $C_1$-$C_4$ alkyl or fluoroalkyl;
 $R_2$ = H or $C_1$-$C_4$ alkyl or fluoroalkyl, in which $R_1$ and $R_2$ can be the same or different;
 $R_3$ = H or $CH_3$;
 $R_4$ = H or $CH_3$, in which $R_3$ and $R_4$ can be the same or different;
 $R_5$ = H;
 $R_6$ = H;
 $R_5,R_6$ ==O(carbonyl);
 $R_7$ = H;
 $R_8$ = a hydrogen bond accepting group.
 $R_7,R_8$ ==O(carbonyl); and
 R′ = an ester group.

6 Claims, 1 Drawing Sheet

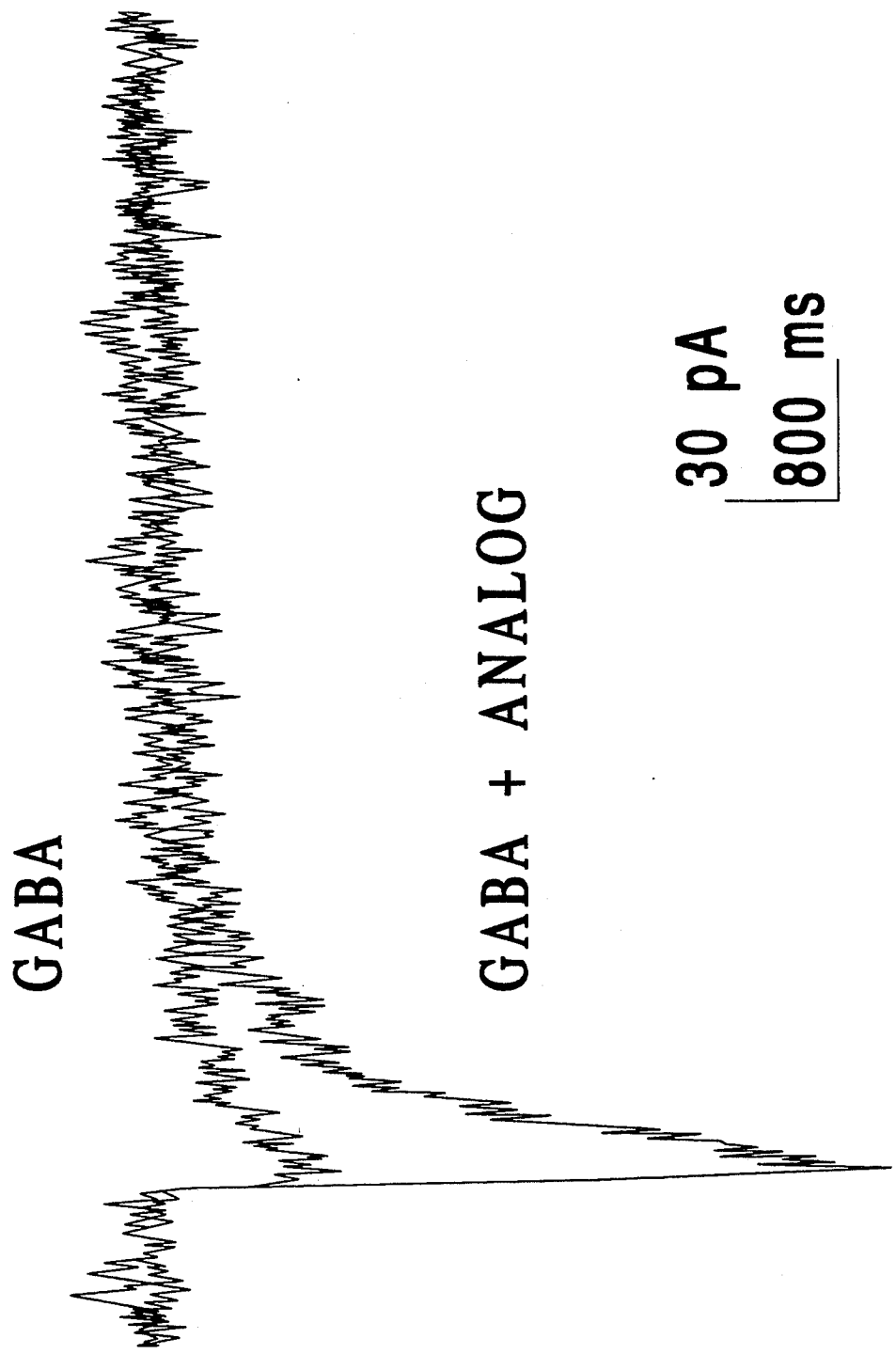

TRICYCLE STEROID ANALOGS

ACKNOWLEDGEMENT OF SUPPORT

The invention herein was made in part with government support under NIH grants HD19746 and NS14834.

This is a division of application Ser. No. 08/004,768, filed Jan. 14, 1993, U.S. Pat. No. 5,292,906 which in turn is a division of application Ser. No. 07/811,208, filed Dec. 20, 1991, now U.S. Pat. No. 5,206,415.

BACKGROUND OF THE INVENTION

This invention relates to novel tricyclic steroid analogs. More particularly, the invention relates to 1H-benz[e]indene dodecahydro compounds that are useful for enhancing gamma-aminobutyric acid (GABA)-reduced chloride currents at the GABA receptor/chloride ionophore complex.

The importance of steroids as crucial components of cellular membranes is well established. Equally well established are the long term endocrine effects of steroid hormones. These endocrine effects are due to binding of steroids to intracellular receptors that subsequently interact with DNA and modulate gene expression. Less well delineated, but currently the subject of increasing interest, are the immediate modulatory effects of certain steroids at ion channels. For example, it is now established that steroid anesthetics, as well as certain endogenously produced metabolites of progesterone and deoxycorticosterone, facilitate GABA's ability to increase neuronal inhibition (for reviews see refs. 10, 15, 25). These steroid effects on GABAergic function have significant pharmacological, physiological, and pathological implications.

GABA is thought to be the major inhibitory neurotransmitter in the vertebrate central nervous system (CNS), exerting actions at two classes of receptors, designated $GABA_A$ and $GABA_B$. These receptors can be distinguished physiologically and pharmacologically (5). $GABA_B$ sites represent the minority of CNS GABA receptors and, based on available studies, are unlikely to be a primary site of action for anesthetic/anticonvulsant drugs. In contrast, $GABA_A$ receptors appear to represent a major site of action for many CNS-active agents and are thought to be a site at which several classes of anesthetics exert their effects. At $GABA_A$ receptors, GABA promotes the direct opening of $Cl^-$-selective ion channels. In most neurons, based on electrochemical gradients, the opening of these channels promotes the influx of $Cl^-$ and produces hyperpolarization of the neuronal membrane. A recurring theme in the GABA literature is that drugs which inhibit $GABA_A$ function, including the competitive antagonist bicuculline and the non-competitive antagonists picrotoxin, t-butylbicyclophosphorothionate (TBPS) and penicillin, act as convulsants whereas agents which augment GABA function, including benzodiazepines and barbiturates, act as anticonvulsants, anesthetics and sedatives (for review see ref. 49).

Consistent with Selye's (42) initial observations that steroids have CNS depressant properties, studies done over the past decade have provided evidence that the anesthetic actions of steroids may occur through enhancement of $GABA_A$-mediated neuronal inhibition. Initial studies demonstrated that alphaxalone, an anesthetic steroid, prolongs the time course of GABA-mediated inhibitory synaptic responses in olfactory cortical slices (39). Subsequent studies using voltage clamp and single channel recording techniques have provided clear evidence that both anesthetic and endogenous steroids can alter $GABA_A$ receptor function in a variety of preparations. In cultured rat hippocampal and spinal cord neurons, anesthetic steroids augment $Cl^-$ currents produced by exogenous GABA (3, 24). Additionally, alphaxalone has been shown to open $Cl^-$ channels directly in the absence of GABA, at concentrations which are relevant to anesthetic effects (3). These steroid gated currents are blocked by bicuculline, suggesting that they are mediated through direct activation of $GABA_A$ receptors, perhaps by an action at the GABA recognition site. In addition to potentiating responses to exogenous GABA, alphaxalone augments inhibitory postsynaptic currents (IPSCs) mediated by $GABA_A$ receptors in cultured hippocampal neurons (14). This effect is manifest as a 5-8 fold prolongation of IPSC decay without change in peak IPSC amplitude or rise time. Taken together, these studies strongly suggest that both by direct $Cl^-$ channel activation and by modulation of GABA-mediated responses anesthetic steroids augment neuronal inhibition through modulation of the $GABA_A$ receptor complex.

The site at which steroids exert these effects remains unclear. Certain actions, including the direct gating of $Cl^-$ channels and the prolongation of IPSC decay are similar to the effects of anesthetic barbiturates (40). In addition, fluctuation analysis experiments have shown that alphaxalone, like the barbiturates, significantly prolongs the burst length of GABA-gated channels without changing the single channel conductance (3). However, recent studies using single channel recordings from recombinant human $GABA_A$ receptors expressed in human embryonic kidney cells have found differences in the actions of barbiturates and endogenous steroid metabolites. Whereas pentobarbital prolongs channel open times and burst lengths, 3α-OH-dihydroprogesterone (DHP) increases the frequency of channel opening without altering the open times (35). Other studies using ligand binding and $Cl^-$ flux measurements have demonstrated additive and synergistic effects of barbiturates and steroids, suggesting separate sites of action (11, 19, 47). Additionally, in bovine adrenal chromaffin cells, steroids greatly potentiate currents induced by high concentrations of pentobarbital (6). This suggests that either steroids and barbiturates act at separate sites in the $GABA_A$ complex or that the effects on GABA-gated responses are mediated by a site that is distinct from the site mediating direct $Cl^-$ channel gating.

An action of steroids at benzodiazepine receptors is less likely as several studies have failed to find an effect of the benzodiazepine antagonist RO15-1788 (flumazenil) on steroid responses (6, 29). Additionally, benzodiazepine agonists potentiate GABA responses by increasing the apparent affinity of GABA for its receptor (7) without altering the single channel properties of the current (45). Benzodiazepine agonists also increase both the duration and amplitude of GABA-mediated IPSCs, an effect which differs from either the steroids or barbiturates (41). Finally, unlike steroids or barbiturates, benzodiazepines do not appear to gate $Cl^-$ channels directly in the absence of GABA.

Further complicating attempts to define the steroid site of action are observations that some steroid analogs inhibit GABA responses. Both pregnenolone sulfate (PS) and dehydroepiandrosterone sulfate (DHEAS) inhibit GABA currents in various CNS neurons (22, 23). However, PS, but not DHEAS, inhibits TBPS binding at the picrotoxin site, suggesting that these two agents may act at separate loci to affect GABA responses. Additionally, PS and picrotoxin have similar single channel effects, decreasing the opening frequency of the channels (27). These observations raise the possibility that the picrotoxin site may be responsible for some steroid actions. Previous studies using alkyl substituted γ-butyrolactones have shown that both potentiation and inhibition of $GABA_A$ responses can be produced by agents acting at the picrotoxin site (16, 17). Interestingly, the γ-butyrolactones appear to alter GABA currents by changing the frequency of channel opening with less effect on the channel open times and no effect on the single channel conductance (2, 48).

Based on the data outlined above, it is clear that anesthetic and endogenous steroids can modulate $GABA_A$ receptor function. However there are several possibilities for the site(s) of action within the complex. The direct $Cl^-$ channel gating may be produced through an action at the GABA recognition site, based on the bicuculline sensitivity of the response. The alteration of responses produced by exogenous GABA and of IPSCs is more likely mediated through an allosteric site. Currently the putative barbiturate and picrotoxin sites are the leading candidates.

Steroid anesthetics were developed by the pharmaceutical industry decades before their effects at GABAergic neurons were established. The steroid anesthetic preparation, Althesin, was considered by anesthesiologists in Europe to have many of the properties desired for an intravenous anesthetic. These favorable properties have been discussed in an editorial by Morgan and Whitman (28). These authors also noted that Althesin was particularly effective and safe for use as an anesthetic in patients with high intracranial pressure resulting from severe head trauma. Unfortunately, Althesin is no longer available to anesthesiologists. It was removed from clinical use because of allergic reactions caused by the solubilizing agent used in the formulation.

Majewska has reviewed the role that steroid modulators of GABAergic function could play in the response to stress (25). Stress causes the release of CRF (corticotropin-releasing factor) from the hypothalamus. CRF in turn causes the release of adrenocorticotropic hormone (ACTH) from the pituitary, and ACTH then stimulates adrenal steroid biosynthesis. Among the adrenal steroids produced are cortisol and deoxycorticosterone. Cortisol has been shown to have biphasic actions at the GABA receptor channel complex found in guinea pig ileum (31). In picomolar concentrations it augments GABA-induced chloride currents, but at nanomolar concentrations it inhibits these same currents. Recent studies (36) support the hypothesis that the elevated concentrations of cortisol resulting from stress-induced increases in ACTH secretion could diminish neuronal inhibition by GABA and enhance the arousal state brought on by stress. Majewska further postulates that these effects may be enhanced by yet another endogenous steroid, pregnenolone sulfate, that she has shown to inhibit GABA-induced chloride currents (22). This sulfated steroid can be made not only in peripheral organs, but also by glial cells in the central nervous system (for a review of brain steroid biosynthesis see ref. 4). Finally, Majewska postulates that the deoxycorticosterone also released from the adrenal gland during stress has an important physiological function. Since deoxycorticosterone can be metabolized to THDOC (5α-pregnane-3α,21-diol-20-one), a steroid known to augment GABA-mediated neuronal inhibition (22), this steroid is postulated to counteract the effects of cortisol at the GABA receptor channel complex and restore homeostasis to the brain during stress.

This ability of endogenous steroids to either decrease or increase GABA-mediated neuronal inhibition has led many investigators (15, 20, 21, 25) to postulate that new steroid derivatives might be useful not only as anesthetics, but also as sedative hypnotics, anxiolytics, anticonvulsants, and antidepressants. In support of these potential uses for synthetic steroid derivatives that could modulate GABAergic function are the following results: 1) THDOC has shown both anxiolytic and sedative activity (different dose/repose curves) in two different animal models of anxiety (8); 2) THDOC has been shown to induce sleep and increase nonREM sleep in rats (26); 3) Saffan (a veterinary formulation of anesthetic steroids) at doses causing neurological symptoms, has been shown to have anticonvulsant activity against both maximal electroshock and chemically-induced seizures (33); and 4) depression is a frequent condition encountered in patients with Cushing's syndrome and it can be treated by lowering the elevated cortisol levels found in these patients (30).

The progesterone metabolite, 3α-OH-DHP (3α-hydroxy-5α-pregnan-20-one), shown below, is also thought to be an important physiologic regulator of GABA-mediated neuronal inhibition. This compound can be made de novo in brain or produced there from circulating progesterone (4). The observation that women having catamenial epilepsy, a condition in which seizure frequency changes during the menstrual cycle, have more seizures when progesterone levels are low during the menstrual cycle has led to the hypothesis that compounds mimicking the actions of 3α-OH-DHP may be useful as anticonvulsants and treatments for premenstrual syndrome (38). The later hypothesis is further supported by the fact that progesterone is often useful for treating premenstrual syndrome (25).

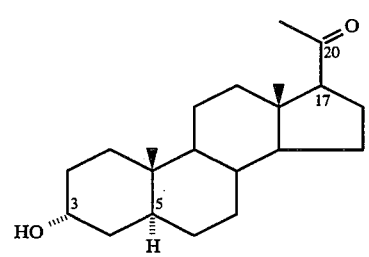

3α-Hydroxy-5α-pregnan-20-one
(3α-OH—DHP)

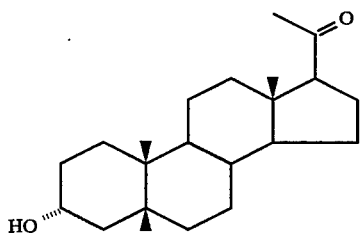

3α-Hydroxy-5β-pregnan-20-one

In summary, the effects of steroid modulation of GABA receptor channel function are highly significant. Steroid-induced hyperpolarization of GABAergic neurons is most likely the mechanism of action of anesthetic steroids. In addition, endogenously produced steroid metabolites of deoxycorticosterone and progesterone may be important physiological modulators of GABA-regulated neuronal inhibition.

Further background information on the structure/activity relationships in steroidal anesthetics can be had by reference to the review article by Phillips (34). Both of the above illustrated compounds, 3α-hydroxy-5α-pregnan-20-one and 3α-hydroxy-5β-pregnan-20-one, are active in vivo as steroid anesthetics according to Phillips. These compounds also are potentiators of muscimol-stimulated chloride uptake in rat synaptoneurosomes (37) and potentiators of GABA-induced chloride currents in electrophysiological experiments (13, 32).

BRIEF DESCRIPTION OF THE INVENTION

In accordance with the present invention, novel tricyclic steroid analogs are provided which are 1H-benz[e]indene dodecahydro compounds. For convenience of presentation, the numbering system and nomenclature rules associated with steroids instead of benz[e]indenes are used herein for description of the invention. Accordingly, these compounds can be represented by the following structural Formulas I and II in the 5α- and 5β-configurations (7α- and 7β-configurations according to the benz[e]indene numbering system), respectively:

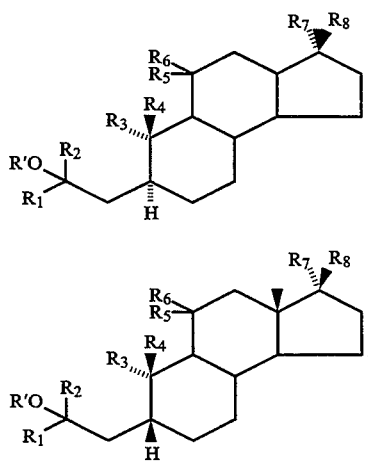

wherein $R_1$ = H or $C_1$–$C_4$ alkyl or fluoroalkyl;

$R_2$ = H or $C_1$–$C_4$ alkyl or fluoroalkyl, in which $R_1$ and $R_2$ can be the same or different;

$R_3$ = H or $CH_3$;

$R_4$ = H or $CH_3$, in which $R_3$ and $R_4$ can be the same or different;

$R_5$ = H;

$R_6$ = H;

$R_5, R_6$ ==O (carbonyl);

$R_7$ = H;

$R_8$ = a hydrogen bond accepting group.

$R_7, R_8$ ==O (carbonyl); and $R'$ = an ester group.

In the above Formulas I and II, the preferred hydrogen bond accepting groups are as follows:

1) ketones (—CO—R″, where R″ can be alkyl or fluoroalkyl groups $C_1$ to $C_4$ or cycloalkyl groups $C_3$ to $C_6$).

2) an α-hydroxy ketone (—CO—CH$_2$OH) or esters thereof (—CO—CH$_2$OXOR‴, where X=C, P=O-(OR‴), or S=O; where R‴ can be alkyl groups $C_1$ to $C_{20}$).

3) alkyl esters of carboxylic acids (—COOR‴, —CH$_2$COOR‴, where R‴ can be alkyl groups $C_1$ to $C_{20}$).

4) amines (NMR″ and N(R″)$_2$ where R″ can be alkyl or fluoroalkyl groups $C_1$ to $C_4$ or cycloalkyl groups $C_3$ to $C_6$).

5) a nitrile (CN)

6) a γ-lactone

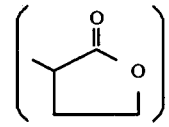

The ester group (R′) can be any group derived from reaction between the hydroxyl group with a $C_1$–$C_{18}$ organic acid, acid halide, anhydride, or ester, such as, e.g., acetic, propionic, n- and i-butyric, n-, i-, s-, and t-valeric, hexanoic, heptanoic, octanoic, nonanoic, decanoic, undecanoic, dodecanoic, palmitic, stearic, cinnamic, benzylic, benzoic, maleic, fumaric, ascorbic, succinic, oxalic, tartaric, citric, gluconic, itaconic, aspartic, and the like.

The preferred configuration is the 5α-configuration of Formula I.

The most preferred compounds of Formula I are the four compounds which can be represented by the following structural Formula III:

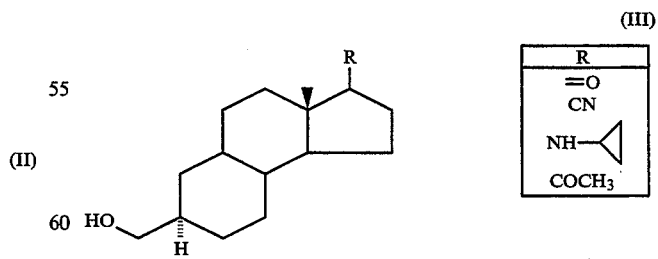

These novel 1H-benz[e]indene dodecahydro compounds have been biologically evaluated on currents gated by 1 μM GABA, and the responses compared to effects produced by 3α-OH-DHP, a neurosteroid known to augment GABA responses. These compounds exhibit reversible GABA potentiating effects at 1 μM and three of the preferred four compounds enhance GABA currents to a greater extent than 3α-OH-DHP.

The compounds of the invention are useful for treating disorders which can be ameliorated by increasing neuronal inhibition via modulation of GABA-regulated chloride channels. Thus, the compounds have utility as anxiolytics, anticonvulsants, sedative hypnotics, and agents to treat premenstrual syndrome. The compounds may also be useful as anesthetics. The compounds are formulated according to conventional methods, and may be administered systematically by injection subcutaneously, intravenously, or intraperitoneally, as well as by oral or transdermal administration. The pharmaceutical compositions containing these compounds will, of course, depend on the route of administration.

Parenteral administration is generally characterized by injection, whether subcutaneously, intramuscularly, or intravenously. Injectables can be prepared in conventional forms, either as solutions or suspensions, in solid forms suitable for solution or suspension in liquid prior to injections or as emulsions. Suitable excipients include water, saline, dextrose, glycerol, and the like. If desired, the pharmaceutical compositions may also include minor amounts of nontoxic auxiliary substances, such as wetting or emulsifying agents, pH-buffering agents, and so forth.

For oral administration, the active ingredient is generally administered as a syrup, capsule, or tablet and pharmaceutically nontoxic compositions are formed using the normally employed excipients, such as pharmaceutical grades of mannitol, lactose, starch, magnesium stearate, talcum, cellulose, magnesium carbonate, and so forth. The compositions include sustained release formulations and contain about 10–95% active ingredient with the remainder carrier, as a general rule.

For administration via suppository, conventional binders and carriers include, for example, polyalkylene glycols or triglycerides, and the suppositories generally contain active ingredient in the range of about 0.5–10%. Standard methods of formulating compounds for administration as pharmaceuticals can be found in Remington's Pharmaceuticals Sciences, Mack Publishing Company, Easton, Pa., latest edition.

The amount of active compound to be administered depends on the subject being treated, the severity of the condition being treated, the manner of administration, and the judgment of the physician. However, an effective dose is in the range of about 0.5–500 mg/day per typical subject.

DETAILED DESCRIPTION OF THE INVENTION

While the specification concludes with claims particularly pointing out and distinctly claiming the subject matter regarded as forming the invention, it is believed that the invention will be better understood from the following description of preferred embodiments taken in conjunction with the accompanying drawing in which:

FIG. 1 shows the modulation of GABA currents by a representative example of the tricyclic steriod analogs of the invention. Shown is the effect of the analog prepared in Example 13 and Table 1, below, in which R=COCH₃ on currents induced by 1 μM GABA. Neurons were voltage clamped at −50 mV, and the test compound administered at 1 μM.

The synthesis of the preferred compounds of generic Formulas I and II is conveniently shown in the following Reaction Schemes 1 and 2. The synthetic method in Reaction Scheme 1 comprises a series of steps to open the A-ring of the known and readily available steroid, 19-nortestosterone, and remove the $C_1$ and $C_2$. The lithium, liquid ammonia reaction carried out in the first step yields the 5α-configuration at the A/B ring fusion (9). Each of the steps carried out in Reaction Scheme 1 is carried out in high yield. Whenever more than one transformation is indicated on an arrow between structures, the yield reported is the overall yield for the combined transformations. Each of the compounds shown in the Reaction Scheme 1 has been purified to homogeneity by chromatographic methods. These compounds have been shown to have the correct elemental composition by combustion analysis and have been characterized by infrared and NMR spectroscopy.

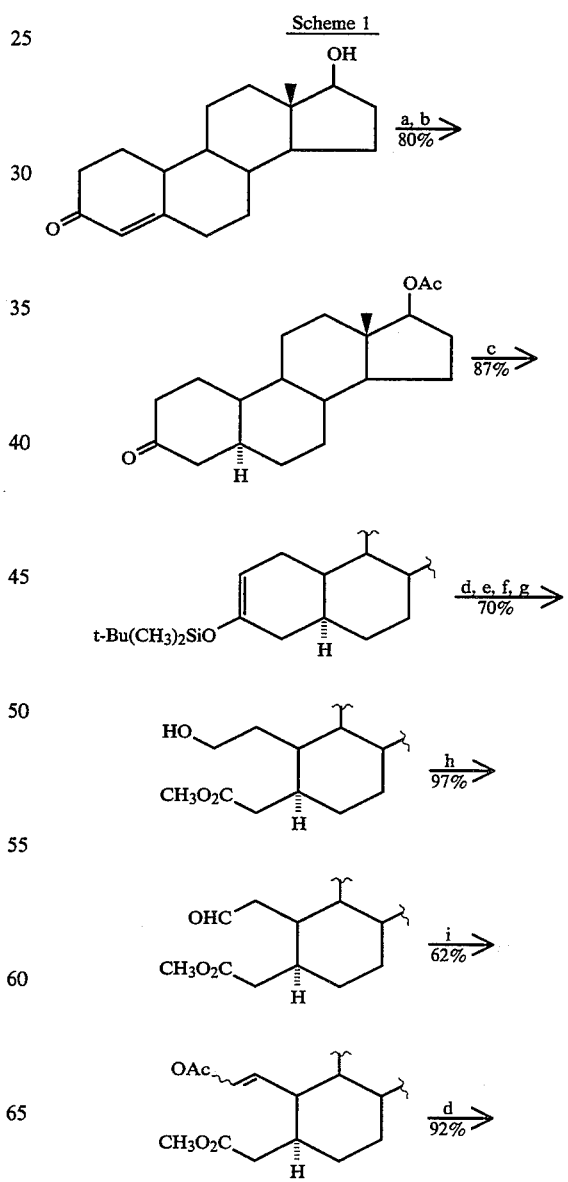

-continued
Scheme 1

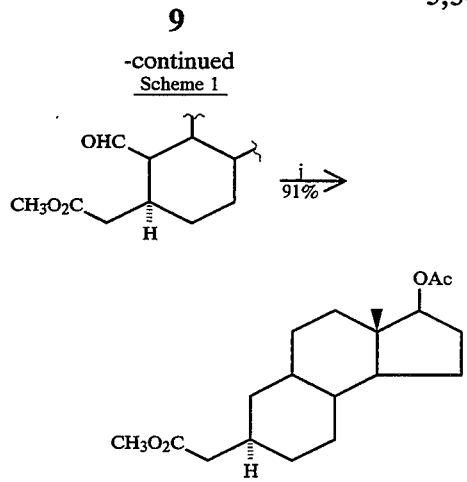

a) Li, liq. NH₃;

duced in the TosMIC reaction (step c) is introduced with ca. 70% 17β-stereochemistry. The 17α-cyano isomer was removed by chromatography.

Finally, in order to synthesize the 5β-analogs, two additional steps not shown in Reaction Scheme 1 are carried out as shown below. The effect of these two steps is to change the side chain from the 5α-configuration to the 5β-configuration. The final compound shown in Reaction Scheme 1 is converted by an α-phenylselenylation/elimination reaction into the α,β-unsaturated ester (43). Catalytic hydrogenation using palladium in tetrahydrofuran and hydrobromic acid is then carried out to give the 5β-reduced tricyclic analog. These conditions are analogous to the conditions known to convert 19-nortestosterone to 5β-dihydrotestosterone with 98% stereospecificity (46). Chromatographic methods can be used to separate mixtures of the 5α and 5β-compounds.

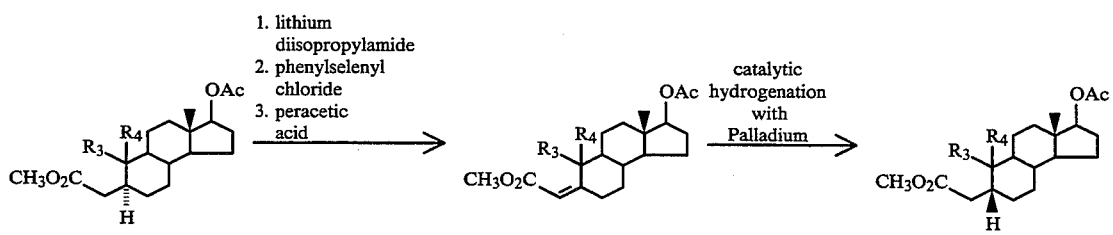

Scheme 2

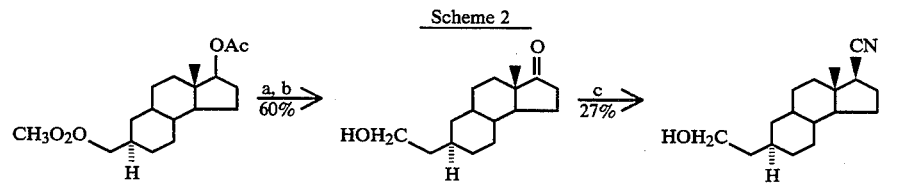

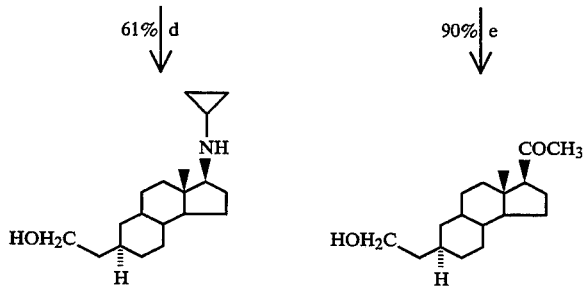

a) DIBAL—H, CH₂CH₂, 20°;
b) NaOCl, HOAc;
c) TosMIC, KOC(CH₃)₃, DME;
d) cyclopropylamine, NaBH₃CN, CH₃OH;
e) CH₃MgI, EtOEt.

b) Ac₂O, Pyr, 100° C.;
c) t-Bu(CH₃)₂SiOTf;
d) O₃, CH₃OH, CH₂Cl₂, −78° C.;
e) NaBH₄;
f) Na₂CO₃, aq. THF;
g) CH₂N₂, Et₂O;
h) PCC, NaOAc, CH₂Cl₂;
i) AcO(CH₃)C=CH₂, p-TsOH;
j) Wilkinson's cat., C₆H₅CN.

Reaction Scheme 2 details the remaining steps needed to prepare various 5α-analogs having the different hydrogen bond acceptor groups (i.e., C=O, CN, COCH₃, and cyclopropyl-NH group) of the final compounds. Yields shown under the arrows are yields obtained for the four preferred compounds whose evaluation are set forth in Table 1, hereinafter. The cyano group introduced Additional tricyclic steroid analogs within the scope of Formulas I and II can be prepared by various of the following reaction schemes:

Introduction of $R_1$ and $R_2$ alkyl or fluoroalkyl groups where $R_1 = R_2$ or $R_1$ not $= R_2$ can be prepared as follows:

Example 7

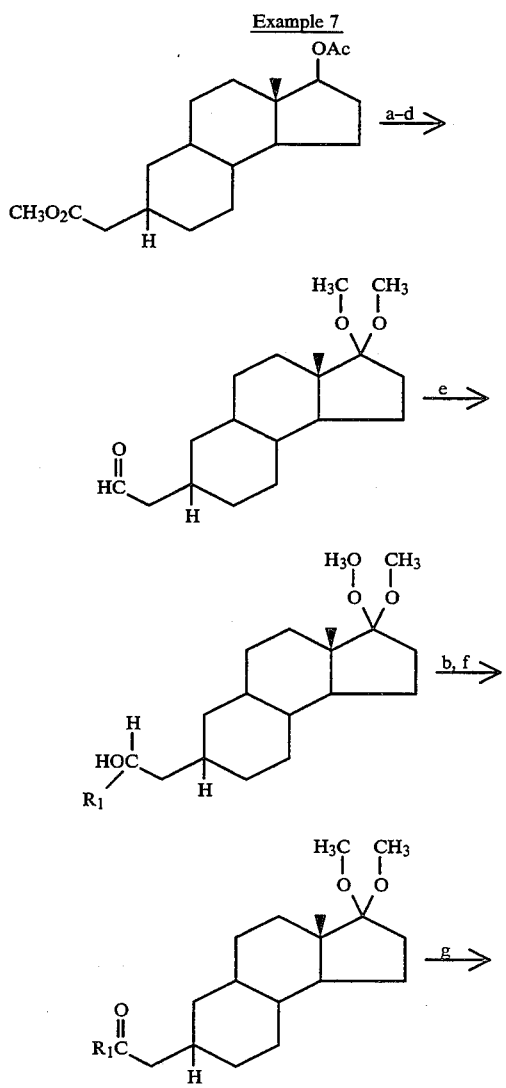

a) NaOH, aq. CH$_3$OH;
b) H$_2$CrO$_4$, acetone;
c) CH$_3$COCl, CH$_3$OH, 50° C.;
d) DIBAL—H, CH$_2$CH$_2$, −78° C.;
e) R$_1$MgBr or (CH$_3$)$_3$SiCF$_3$ (when R$_1$ = CF$_3$);
f) R$_2$MgBr;
g) acetone, aq. H$_2$SO$_4$.

Examples show preparation of compounds where R$_3$=R$_4$=H or R$_3$=H and R$_4$=CH$_3$ preparation of compounds where R$_3$=CH$_3$ and R$_4$=H or CH$_3$ is as follows:

Example 4

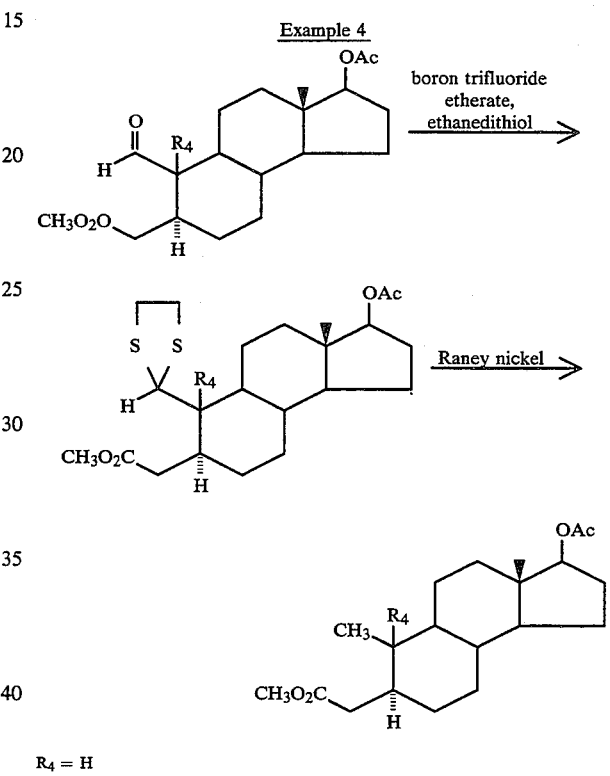

R$_4$ = H

Compounds having R$_5$, R$_6$= =O could be prepared by starting with materials having a ketone at the 11-position. For example:

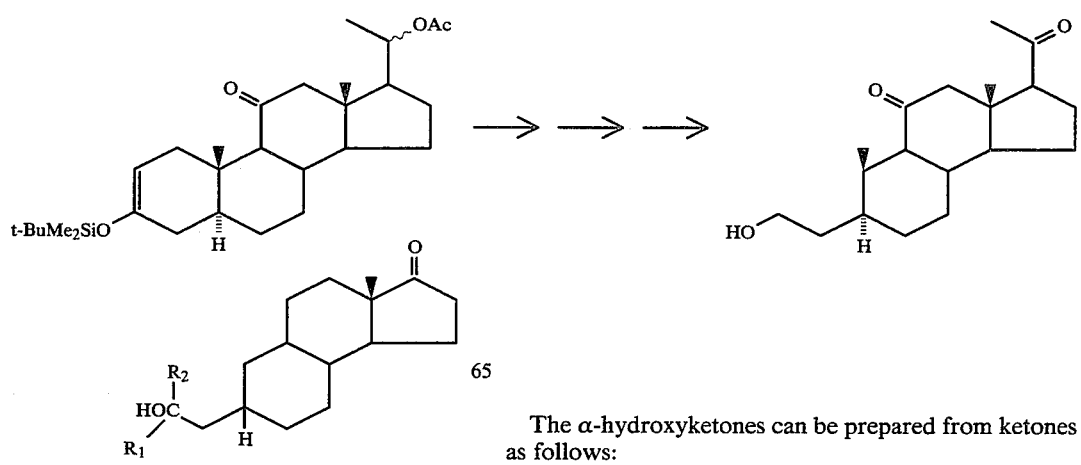

The α-hydroxyketones can be prepared from ketones as follows:

Example 13

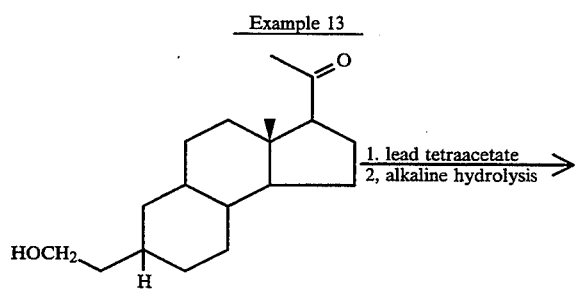

The various derivatives of the α-hydroxyketone are prepared as follows:

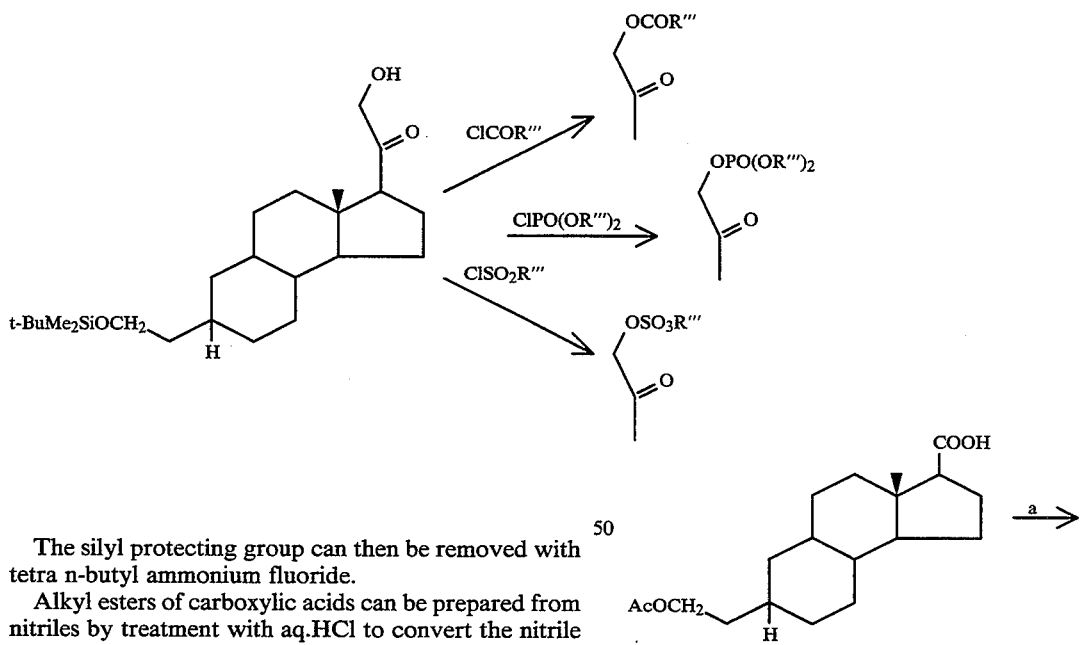

The silyl protecting group can then be removed with tetra n-butyl ammonium fluoride.

Alkyl esters of carboxylic acids can be prepared from nitriles by treatment with aq.HCl to convert the nitrile group to the carboxylic acid group, and then esterifying the carboxylic acid with dry HCl in the appropriate alkanol.

Example 12

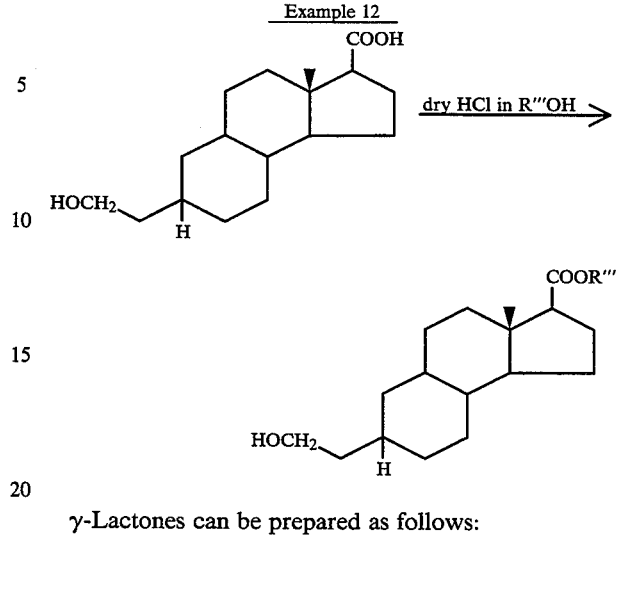

γ-Lactones can be prepared as follows:

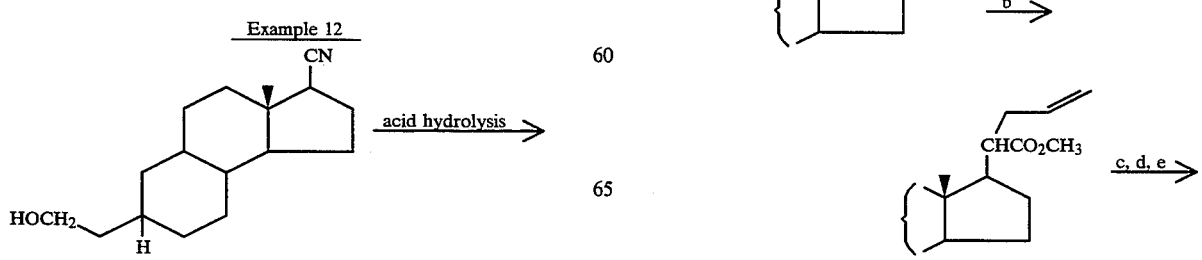

-continued

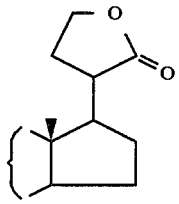

a) Ardnt-Eistert Reaction;
b) alkylation with allyl bromide;
c) ozonolysis;
d) sodium borohydride reduction;
e) acidification The following detailed Examples will further illustrate the invention although it will be understood that the invention is not limited to these specific Examples or the details described therein.

As indicated in structural Formulas I and II, R$_4$ can be H or CH$_3$. The following are general structures of compounds prepared in the following specific examples in which R can be H or CH$_3$.

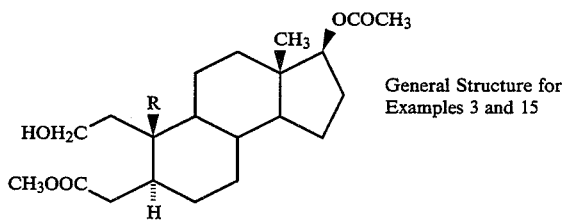

General Structure for Examples 3 and 15

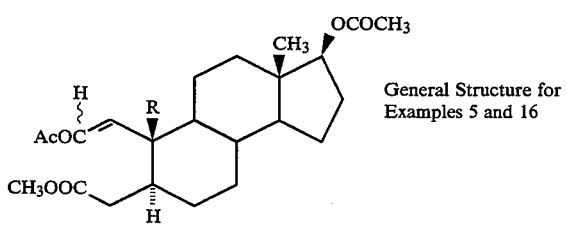

General Structure for Examples 5 and 16

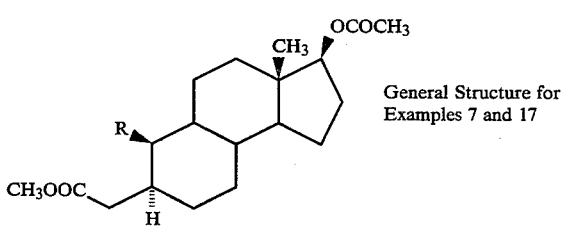

General Structure for Examples 7 and 17

EXAMPLE 1

Preparation of 3-[[(1,1-Dimethylethyl)dimethylsilyl]oxy]-5α-estran-17β-ol acetate To a solution of 17β-acetyloxy-5α-estran-3-one (1.595 g, 5 mmol) in dry dichloromethane (30 mL) was added with stirring at ice-water bath temperature, triethyl amine (2 mL) followed by t-butyldimethylsilyl triflate (2.64 g, 10 mmol). The solution was stirred for 25 min, then diluted with dichloromethane (20 mL) and washed with satd.aq. NaHCO$_3$ (30 mL), brine (30 mL) and dried over Na$_2$SO$_4$. The solvent was removed to yield a solid, which was purified by chromatography (silica gel, dichloromethane, pretreated with 1% triethyl amine in hexanes) to get 1.9 g (87%) of pure product as colorless crystals, m.p. 89°–90° C.

IR (film, NaCl): 2927, 2858, 1739, 1676, 1472, 1371, 1246 cm$^{-1}$.

$^1$H NMR (CDCl$_3$): δ 4.80 (dd, 1H, CH=C), 4.59 (dd, 1H, CHOAc), 2.04 (s, 3H, COCH$_3$), 0.91 (s, 9H, (CH$_3$)$_3$C), 0.80 (s, 3H, CH$_3$), 0.11 (s, 6H, (CH$_3$)$_2$Si).

$^{13}$C NMR(CDCl$_3$): δ 171.58 (CH$_3$COO), 149.88 (C$_3$), 103.48 (C$_2$), 82.97 (C$_{17}$), 25.51 (((CH$_3$)$_3$C), 11.81 (C$_{18}$), −4.62 and −4.78 ((CH$_3$)$_3$CSi and (CH$_3$)$_2$Si).

Elemental Analysis: For C$_{26}$H$_{44}$O$_3$Si. Calcd: C, 72.17; H, 10.25; Found: C, 72.49; H, 10.06.

Structure:

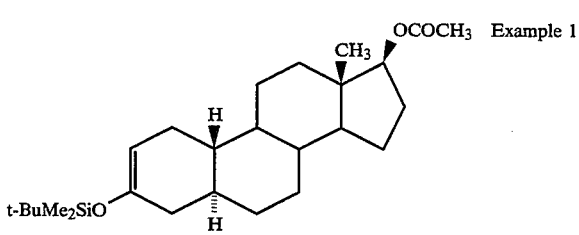

EXAMPLE 2

Preparation of [3S-(3α,3aα,5aβ,6β,7α,9aα,9bβ)]-3-(Acetyloxy)-dodecahydro-6-(2-hydroxyethyl)-3a-methyl-1H-benz[e]indene-7-acetic acid A solution of the silyl ether of Example 1 (0.866 g, 2 mmol) in dichloromethane (10 mL) and methanol (10 mL) was treated with O$_3$ at −78° C. until a blue color persisted. Excess O$_3$ was discharged by O$_2$ stream. NaBH$_4$ (1.0 g) was added with stirring. The mixture was allowed to react at −78° C. for 1 h and at room temperature for 1.0 h, then the mixture was diluted with diethyl ether (25 mL) and poured into cooled 10% aq.HCl solution (250 mL). The organic phase was washed with water (25 mL), brine (25 mL), and dried over Na$_2$SO$_4$. The solvent was removed on a rotary evaporator to give a viscous liquid, which was diluted with n-hexane to give a colorless solid. Another portion of product was obtained by evaporating the n-hexane solution and hydrolyzing the residue with a mixture consisting of 10% aq. K$_2$CO$_3$ (10 mL), tetrahydrofuran (15 mL), and methanol (30 mL) for 1.5 h at room temperature. The crude compound was recrystallized from methanol to give 0.49 g (70%) pure compound as colorless crystals, m.p. 141°–145° C.

IR (film, NaCl): 3328, 2918, 2850, 1732, 1705, 1444, 1732, 1246 cm$^{-1}$.

$^1$H NMR (CDCl$_3$): δ 4.59 (t, J=8.4 Hz, 1H, CHOAc), 3.56–3.69 (m, 2H, CH$_2$OH), 2.62 (dd, J=15.8, J=2.6 Hz, 1H of CH$_2$COOH), 2.05 (s, 3H, OCOCH$_3$), 0.80 (s, 3H, CH$_3$).

$^{13}$C NMR(CDCl$_3$): δ 178.54 (COOH), 171.78 (CH$_3$COO), 82.83 (C$_3$), 59.79 (CH$_2$OH), 11.75 (C$_{3a}$).

Elemental Analysis: For C$_{20}$H$_{32}$O$_5$. Calcd: C, 68.15; H, 9.15; Found: C, 68.01; H, 9.27.

Structure:

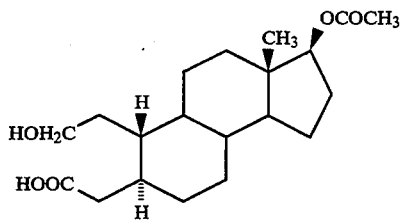

Example 2

EXAMPLE 3

Preparation of Methyl [3S-(3α,3aα,5aβ,6β,7α,9aα,9bβ)]-3-(Acetyloxy)-dodecahydro-6-(2-hydroxyethyl)-3a-methyl-1H-benz[e]indene-7-acetic acid To a solution of 3.52 g (10 mmol) of the compound of Example 2 in diethyl ether (350 mL), diazomethane in diethyl ether was added until a yellow color persisted at 0° C. The solution was allowed to stir for an additional 15 min. Excess diazomethane was destroyed by addition of several drops of formic acid. The mixture was washed with 10% aq. $NaHCO_3$ (100 mL), water (100 mL), and brine (100 mL); and dried over $Na_2SO_4$. The solvent was removed to give a virtually quantitive yield of product, m.p. 72°–73.5° C.

IR (film, NaCl): 3455, 2921, 2873, 1737, 1437, 1373, 1246 $cm^{-1}$.

$^1H$ NMR ($CDCl_3$): δ 4.59 (t, J=7.7 Hz, 1H, CHOAc), 3.68 (s, 3H, $COOCH_3$), 3.68–3.61 (m, 1H, $CH_2OH$), 2.59 (dd, J=15.1 Hz, J=4.1 Hz, 1H of $CH_2COOCH_3$), 2.04 (s, 3H, $OCOCH_3$), 0.80 (s, 3H, $CH_3$).

$^{13}C$ NMR($CDCl_3$): δ 174.47 ($COOCH_3$), 171.55 ($CH_3COO$), 82.75 ($C_3$), 60.02 ($CH_2OH$), 51.3 ($CH_3O$), 11.75 ($C_{3a}$).

Elemental Analysis: For $C_{21}H_{34}O_5$. Calcd: C, 68.82.; H, 9.35; Found: C, 68.78; H, 9.65

Structure:

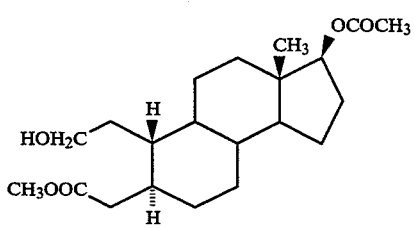

Example 3

EXAMPLE 4

Preparation of Methyl [3S-(3α,3aα,5aβ,6β,7α,9aα,9bβ)]-3-(Acetyloxy)-dodecahydro-6-(2-oxoethyl)-3a-methyl-1H-benz[e]indene-7-acetic acid To a stirring suspension of pyridinium chloroformate (0.65 g, 3.0 mmol) and anhydrous NaOAc (0.25 g, 3.0 mmol) in dry dichloromethane (50 mL) was added a solution of the compound of Example 3 (0.73 g 2.0 mmol) in dry dichloromethane (10 mL) at room temperature under nitrogen. After the mixture was stirred for 2 h, diethyl ether (40 mL) was added. The mixture was filtered with a Bushier filter which was filled with silica gel and washed with dichloromethane. The solvent was removed to get a solid which was recrystallized from diethyl ether to give 0.70 g (96.7%) pure product as colorless crystalline needles, m.p. 105°–107° C.

IR (film, NaCl): 2923, 2854, 2721, 1737, 1734, 1437, 1374, 1246 $cm^{-1}$.

$^1H$ NMR ($CDCl_3$): δ 9.82 (t, J=1.6 Hz, 1H, CHO), 4.59 (t, J=8.0 Hz, 1H, CHOAc), 3.67 (s, 3H, $COOCH_3$), 2.04 (s, 3H, $OCOCH_3$), 0.80 (s, 3H, $CH_3$).

$^{13}C$ NMR ($CDCl_3$): δ 202.48 (CHO), 173.60 ($COOCH_3$), 171.40 ($CH_3COO$), 82.53 ($C_3$), 11.69 ($C_{3a}$).

Elemental Analysis: For $C_{21}H_{32}O_5$. Calcd: C, 69.20; H, 8.85; Found: C, 69.05, H, 8.78.

Structure:

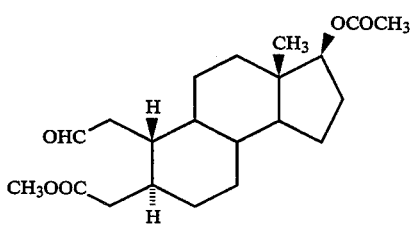

Example 4

EXAMPLE 5

Preparation of Methyl [3S-(3α,3aα,5aβ,6β,7α,9aα,9bβ)]-3-(Acetyloxy)-6-[2E-(acetyloxy)ethenyl]dodecahydro-3a-methyl-1H-benz[e]indene-7-acetic acid A solution of the compound of Example 4 (20 g, 55 mmol) and p-tolulenesulfonic acid (1.0 g, 5% w/w) in isopropenyl acetate (500 mL) was gently distilled for 2.0 h and about 25 mL of solution was collected. After refluxing for 14 h, the mixture was gently distilled for another 2.0 h and about 25 mL of solution again was collected. The reaction mixture was cooled to room temperature and poured into dichloromethane (500 mL), and washed with water (100 mL), satd aq. $NaHCO_3$ (100 mL), and water (100 mL). The organic layer was dried over $Na_2SO_4$, filtered, and concentrated to give a yellow oil, which was chromatographed (silica gel, eluting with 4:1-hexane:ethyl acetate) to give 14 g (62%) pure product as colorless crystals, m.p. 122°–123° C.

IR (film, NaCl): 2920, 1750, 1738, 1737, 1673 1436, 1372, 1226 $cm^{-1}$.

$^1H$ NMR ($CDCl_3$): δ 7.01 (d, J=12.5 Hz, 1H, AcOCH=CH), 5.01 (dd, J=12.5 Hz, J=10.7 Hz, 1H, AcOCH=CH), 4.59 (t, J=7.8 Hz, 1H, CHOAc), 3.63 (s, 3H, $COOCH_3$), 2.49 (dd, J=15.4 Hz, J=4.4 Hz, 1H of $CH_2COOCH_3$), 2.04 (s, 3H, $OCOCH_3$), 0.79 (s, 3H, $CH_3$).

$^{13}C$ NMR ($CDCl_3$): δ 174.09 ($COOCH_3$), 171.50 ($CH_3COOCH$), 168.32 ($CH_3COOCH=$), 136.35 (OCH=), 117.35 (=CH), 82.67 ($C_3$), 11.80 ($C_{3a}$).

Elemental Analysis: For $C_{23}H_{34}O_6$. Calcd: C, 67.96; H, 8.43. Found: C, 68.24; H, 8.53.

Structure:

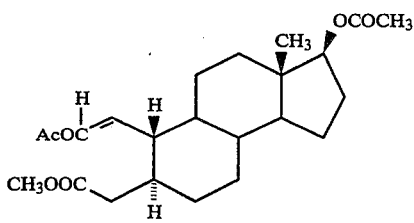

Example 5

EXAMPLE 6

Preparation of Methyl [3S-(3α,3aα,5aβ,6β,7α,9aα,9bβ)]-3-(Acetyloxy)-6-formyldodecahydro-3a-methyl-1H-benz[e]indene-7-acetic acid A solution of the compound of Example 5 (0.81 g, 2.0 mmol) in dichloromethane (50 mL) and acetic acid (0.5 mL) was cooled to $-78°$ C. in an acetone-dry ice bath and treated with $O_3$ until a blue color persisted. The excess $O_3$ was removed by bubbling $O_2$. Methyl sulfide (4 drops, ca. 4.0 mmol) was added and the mixture was stirred for 1.0 h at $-78°$ C. and 1.0 h at the room temperature. The mixture was diluted with dichloromethane (50 mL) and the organic layer was washed with water (50 mL), satd.aq. $NaHCO_3$ (50 mL), water (2×50 mL) again; and dried over $Na_2SO_4$. The organic solvent was removed to give a solid, which was recrystallized from diethyl ether to give 0.64 g (92%) of product as colorless crystals, m.p. 123°-124° C.

IR (film, NaCl): 2924, 2870, 2805, 2707, 1738, 1735, 1721, 1436, 1372, 1244 $cm^{-1}$.

$^1H$ NMR ($CDCl_3$): δ 9.44 (d, J=5.4 Hz, 1H, CHO), 4.62 (t, J=8.5 Hz, 1H, CHOAc), 3.66 (s, 3H, $COOCH_3$), 2.04 (s, 3H, $OCOCH_3$), 0.80 (s, 3H, $CH_3$).

$^{13}C$ NMR ($CDCl_3$): δ 205.44 (CHO), 172.88 ($COOCH_3$), 171.38 ($CH_3COO$), 82.41 ($C_3$), 11.71 ($C_{3a}$).

Elemental Analysis: For $C_{20}H_{30}O_5$. Calcd: C, 68.55; H, 8.63; Found: C, 68.71; H, 8.81.

Structure:

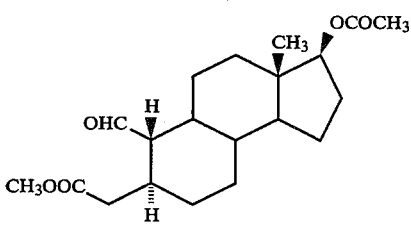

Example 6

EXAMPLE 7

Preparation of Methyl [3S-(3α,3aα,5aβ,7α,9aα,9bβ)]-3-(Acetyloxy)dodecahydro-3a-methyl-1H-benz[e]indene-7-acetic acid The mixture of the compound of Example 6 (0.70 g, 2.0 mmol) and Wilkinson's catalyst (1.85 g, 2.0 mmol) in benzonitrile (30 mL) was heated to 160° C. for 20 h under nitrogen. Most of the benzonitrile was removed by distillation and a mixture of ethyl acetate and hexane (1:1 v/v, 50 mL) was added to precipitate the organometallic by-product. The yellow solid was filtered and the solid was washed with cold ethyl acetate (2×20 mL). The combined organic layer was evaporated to give a viscous liquid, which was chromatographed (silica gel, 1% acetonitrile in dichloromethane) to give 0.59 g (91%) pure product as slightly yellow crystals, m.p. 61°-62° C.

IR (film, NaCl): 2918, 2851, 1741, 1738, 1446, 1373, 1246 $cm^{-1}$.

$^1H$ NMR ($CDCl_3$): δ 4.61 (t, J=8.5 Hz, 1H, CHOAc), 3.67 (s, 3H, $COOCH_3$), 2.04 (s, 3H, $OCOCH_3$), 0.80 (s, 3H, $CH_3$).

$^{13}C$ NMR ($CDCl_3$): δ 173.74 ($COOCH_3$), 171.44 ($CH_3COO$), 82.72 ($C_3$), 11.85.($C_{3a}$).

Elemental Analysis: For $C_{19}H_{30}O_4$. Calcd: C, 70.77; H, 9.38; Found: C, 70.68; H, 9.33.

Structure:

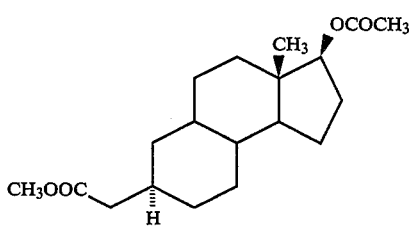

Example 7

EXAMPLE 8

Preparation of [3S-(3α,3aα,5aβ,7α,9aα,9bβ)]-Dodecahydro-3-hydroxy-3a-methyl-1H-benz[e]indene-7-acetic acid To a solution of the compound of Example 7 (100 mg, 0.38 mmol) in methanol (10 mL) was added an aq. solution of NaOH (0.19 g in 2 mL water). After stirring at room temperature for 18 h, aq. HCl (6N, 20 mL) was added, and the reaction mixture was poured into water (100 mL). The product precipitated and was recovered as a white solid by filtration. It was recrystallized from aq. methanol to give 67 mg (81% yield) pure product as fine white crystals, m.p. 202°-203° C.

IR (film, AgCl): 3401, 2895, 1703, 1338, 1233, 1056 $cm^{-1}$.

$^1H$ NMR ($CDCl_3$): δ 3.66 (t, J=8.3 Hz, 1H, CHOH), 2.24 (d, J=6.8 Hz, 1H of $CH_2COOH$), 0.75 (s, 3H, $CH_3$),

Elemental Analysis: For $C_{16}H_{26}O_3$. Calcd: C, 72.14; H, 9.84; Found: C, 71.91; H, 9.62.

Structure:

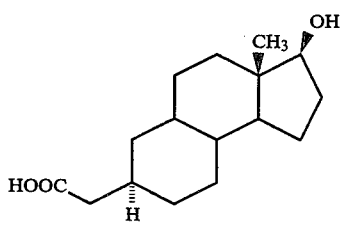

Example 8

EXAMPLE 9

Preparation of [3S-(3α,3aα,5aβ,7α,9aα,9bβ)]-Dodecahydro-3-hydroxy-3a-methyl-1H-benz[e]indene-7-ethanol To a stirred, cooled (ice-water bath) solution of the compound of Example 7 (0.65 g, 2.0 mmol) in dry toluene (50 mL) was added diisobutyl aluminium hydride (1.0M solution in toluene, 12 mL, 12 mmol). After 3.0 h, toluene-methanol (1:1, 4 mL) was added and followed by 10% aq. HCl (10 mL). Then the mixture was washed with water (2×50 mL) and brine (50 mL). The organic layer was dried over Na₂SO₄, filtered and concentrated under reduced pressure to give a solid, which was recrystallized from ethyl alcohol to yield 0.47 g (93%) of pure product as colorless crystals, m.p. 145°–147° C.

IR (film, NaCl): 3279, 2914, 2870, 2858, 2841, 1469, 1443, 1381, 1348, 1067, 1056 cm⁻¹.

¹H NMR (CDCl₃): δ 3.73–3.65 (m, 3H, CH₂OH and CHOH), 0.76 (s, 3H, CH₃).

¹³C NMR (CD₃OD): δ 82.63 (C₃), 60.78 (CH₂OH), 11.71 (C₃ₐ).

Elemental Analysis: For C₁₆H₂₈O₂. Calcd: C, 76.14; H, 11.18; Found: C, 75.96; H, 11.29

Structure:

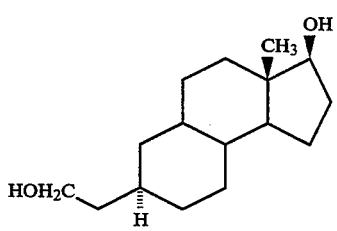

Example 9

EXAMPLE 10

Preparation of
[3aS-(3aα,5aβ,7α,9aα,9bβ)]-7-(2-Hydroxyethyl)-dodecahydro-3a-methyl-3H-benz[e]inden-3-one To a stirred solution of the compound of Example 9 (254 mg, 1.0 mmol) in glacial acetic acid (5 mL) was added dropwise a 5.25% solution of sodium hypochlorite (1.5 mL, 1.05 mmol) at room temperature over 10 min. After the stirring was continued for another 1.0 h, isopropanol (2.0 mL) was added to quench any excess oxidant, followed by water (5.0 mL). The mixture was extracted with ethyl acetate (2×25 mL). The combined organic layer was washed with water (25 mL), satd. aq NaHCO₃ (25 mL), water (25 mL), and brine; (25 mL) and dried over Na₂SO₄. The solvent was removed to give an oil, which was purified by column chromatography (silica gel, eluted with 1:1 ethyl acetate-hexane) to give 161 mg (64%) of pure product as colorless crystals (from diethyl ether-hexane), m.p. 38°–40° C.

IR (film, NaCl): 3435, 2917, 1739, 1452, 1406, 1373, 1258, 1097, 1046, cm⁻¹.

¹H NMR (CDCl₃): δ 3.71 (t, J=6.5 Hz, 2H, CH₂OH), 0.87 (s, 3H, CH₃).

¹³C NMR (CDCl₃): δ 222.05 (CO), 60.07 (CH₂OH), 13.44 (C₃ₐ).

Elemental Analysis: For C₁₆H₂₆O₂. Calcd: C, 76.75; H, 10.47; Found: C, 76.52; H, 10.24

Structure:

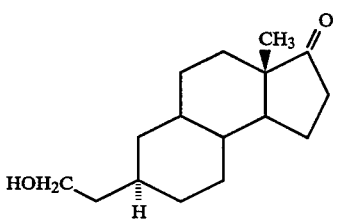

Example 10

EXAMPLE 11

Preparation of
[3S-(3α,3aα,5aβ,7α,9aα,9bβ)]-7-(2-Hydroxyethyl)-dodecahydro-3a-methyl-1H-benz[e]indene-3-cyclopropylamine To a solution of anhydrous cyclopropylamine (170 mg, 3.0 mmol) in absolute methanol (10 mL) was added a solution of the compound of Example 10 (150 mg, 0.6 mmol) in methanol (5.0 mL) and then NaBH₃CN (62 mg, 1.0 mmol) at room temperature under nitrogen. The pH value of the mixture was adjusted to equal about 6 with methanolic HCl solution. After the mixture was stirred for 72 h at room temperature, the solvent was evaporated under vacuum and the residue was dissolved in 6N aq.HCl and extracted with diethyl ether (3×25 mL). The solution was made basic with satd. NaOH solution and was saturated with NaCl. The free amine crystallized on the surface of the solution and was extracted with diethyl ether (3×50 mL). The combined solutions were evaporated. The residue was dissolved in methanol (10 mL) and bubbled with HCl gas until strongly acidic. Most of the methanol was removed under vacuum to give a residue which was recrystallized from methanol-ethyl acetate-hexane to give 120 mg (61%) of pure product as colorless crystalline needles, m.p. 220°–222° C.

IR (KBr): 3400, 3379, 3051, 2918, 2845 2795, 2732, 1591 1446, 1052, 1036 cm⁻¹.

¹H NMR (CD₃OD) δ 3.52 (t, J=6.5 Hz, 2H CH₂OH), 0.83 (s, 3H, CH₃).

¹³C NMR (CD₃OD): δ 70.39 (C₃), 60.70 (CH₂OH), 12.28 (C₃ₐ).

Elemental Analysis: For C₁₉H₃₄ClNO. Calcd: C, 69.59; H, 10.45; N, 4.27; Cl, 10.81. Found: C, 69.46; H, 10.47; N, 4.24; Cl, 11.00.

Structure:

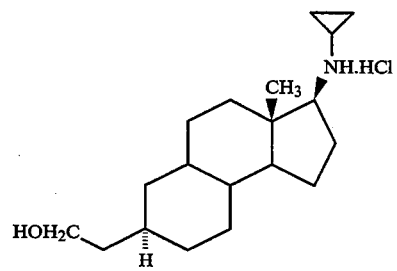

Example 11

EXAMPLE 12

Preparation of
[3S-(3α,3aα,5aβ,7α,9aα,9bβ)]-7-(2-Hydroxyethyl)-dodecahydro-3a-methyl-1H-benz[e]indene-3-carbonitrile A solution of the compound of Example 10 (320 mg 1.28 mmol) in dimethoxyethane (32 mL) was treated with a 1.0M solution of t-BuOK in dimethoxyethane (12.8 mL, 12.8 mmol) and ethanol (2.0 mL). A solution of tosylmethyl isocyanide (500 mg, 2.56 mmol) in dimethoxyethane (6.5 mL) was added very slowly by means of a syringe over 20 min with stirring at room temperature. After 3.0 h, the mixture was quenched with water (50 mL) and extracted with ethyl acetate (3×50 mL). The organic layers were combined and washed with water (2×50 mL) and brine (50 mL); and dried over Na₂SO₄. The solvent was removed to get an oil, which was purified by chromatography (silica gel, eluted with 10% acetonitrile in dichloromethane) to give 200 mg (60%) of a mixture of 17α- and 17β-nitrile isomers as a colorless oil. $^{13}$C NMR spectra of this mixture showed two peaks at δ 122.22 and δ 121.27 respectively, and their ratio was 38:62. The isomers were separated by HPLC (Ultrasphere-Si, 5 μ, 250 mm column eluted with 30% ethyl acetate in hexane at 3.0 mL/min) to give 90 mg (27%) of pure product (β isomer), which was recrystallized from diethyl ether and hexane as colorless crystals, m.p. 82°-83° C.

IR (Film, NaCl): 3294, 2917, 2853, 2233, 1470, 1384, 1338, 1056, 1021 cm⁻¹.

$^1$H NMR (CDCl₃) δ 3.64–3.61 (m, 2H, CH₂OH), 0.88 (s, 3H, CH₃).

$^{13}$C NMR (CDCl₃): δ 121.43 (CN), 60.30 (CH₂OH), 14.05 (C$_{3a}$).

Elemental Analysis: For C₁₇H₂₇NO. Calcd: C, 78.11; H, 10.41; N, 5.36. Found: C, 78.38; H, 10.26; N, 5.28.

Structure:

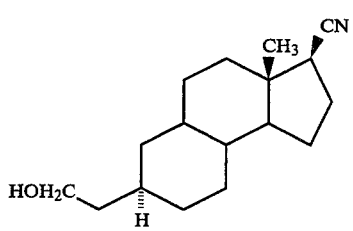

Example 12

EXAMPLE 13

Preparation of [3S-(3α,3aα,5aβ,7α,9aα,9bβ)]-1-[7-(2-Hydroxyethyl)-dodecahydro-3a-methyl-1H-benz[e]inden-3-yl]-ethanone To a solution of methylmagnesium iodide (3.0M solution in diethyl ether, 1.7 mL, 5.0 mmol) was added a solution of the compound of Example 12 (260 mg, 1.0 mmol) in dry tetrahydrofuran (10 mL) at ice-water bath temperature under nitrogen. Then the mixture was refluxed for 24 h. After the reaction was cooled down to 0° C., satd. aq. NH₄Cl solution was added to destroy any excess Grignard reagent. The mixture was extracted with ethyl acetate (3×25 mL). The combined organic layer was dried over Na₂SO₄ and evaporated to give an oil, which was purified by chromatography (10% acetonitrile in dichloromethane) to give 249 mg (90%) of pure product as colorless crystals (from ethyl ether and hexane), m.p. 61°-62° C.

IR (Film, NaCl): 3391, 2916, 1705, 1447, 1384, 1056 cm⁻¹.

$^1$H NMR (CDCl₃) δ 3.69 (t, J=6.6 Hz, 2H, CH₂OH), 2.12 (s, 3H, COCH₃), 0.62 (s, 3H, CH₃).

$^{13}$C NMR(CDCl₃): δ 210.34 (CO), 60.54 (CH₂OH), 13.22 (C$_{3a}$).

Elemental Analysis: For C₁₈H₃₀O₂. Calcd: C, 77.65; H. 10.86; Found: C, 77.68; H, 10.83.

Structure:

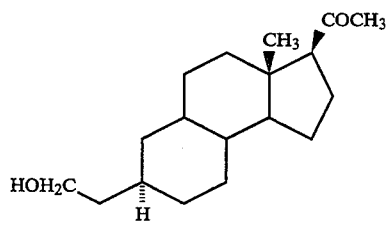

Example 13

EXAMPLE 14

Preparation of [3S-(3α,3aα,5aβ,6β,7α,9aα,9bβ)]-3-(Acetyloxy)-dodecahydro-6-(2-hydroxyethyl)-3a,6-dimethyl-1H-benz[e]indene-7-acetic acid A solution of an approximately 8:2 mixture of 3,17β-diacetoxyandrost-3-ene and 3,17β-diacetoxyandrost-2-ene (9.7 g, 26.9 mmol) in dichloromethane (400 mL) and acetic acid (30 mL) was treated with O₃ at −78° C. until a blue color persisted. Excess O₃ was discharged by an O₂ stream until colorless and then the addition of methyl sulfide (1 drop). The dichloromethane was removed on a rotary evaporator, and water (90 mL) and acetic acid (200 mL) was added to the remaining solution. After stirring overnight to hydrolyze the anhydride group generated during ozonolysis, water (200 mL) and diethyl ether (500 mL) were added. The diethyl ether layer was repeatedly washed with water to remove acetic acid and then dried over MgSO₄. Solvent removal yielded a slightly yellow solid (10.7 g) that was dissolved in methanol (220 mL) cooled to 0° C., and reacted with slowly added portions of NaBH₄ (14.3 g). Fifteen min after NaBH₄ addition was completed, 10% aq. HCl was added until the solution became acidic. Water (250 mL) was added, and methanol removal on a rotary evaporator was accompanied by the precipitation of the steroid product. After filtration and air drying the crude product (8.2 g, 87%) was obtained as a white solid. Recrystillization from methanol yielded the pure product which had m.p. 182°-184.5° C.

IR (film, AgCl) 3319, 1247, 1214, 1729, 1692 cm⁻¹.

$^1$H NMR (CDCl₃) δ 4.58 (t, J=10.8 Hz, 1H, CHOAc), 3.72 (m, 2H, CH₂OH), 2.62 (d, J=12.9 Hz, 1H of CH₂COOH), 2.04 (s, 3H, OCOCH₃), 0.77 (s, 6H, CH₃(C$_{3a}$) and CH₃ (C₆)).

Elemental Analysis: For C₂₁H₃₄O₅. Calcd: C, 68.92; H, 9.35. Found: C, 69.29; H, 9.29.

Structure:

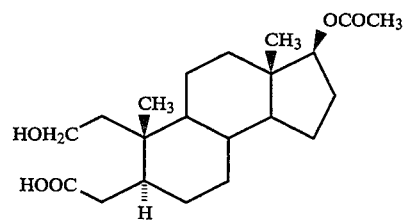

Example 14

EXAMPLE 15

Preparation of Methyl [3S-(3α,3aα,5aβ,6β,7α,9aα,9bβ)]-3-(Acetyloxy)-dodecahydro-6-(2-hydroxyethyl)-3a,6-dimethyl-1H-benz[e]indene-7-acetic acid To a solution of 5.4 g (17.8 mmol) of the compound of Example 14 in diethyl ether (150 mL), diazomethane in diethyl ether was added until a yellow color persisted. The solution was allowed to stir for an additional 15 min. Excess diazomethane was destroyed by addition of several drops of formic acid. The solvent was removed on a rotary evaporator and the crude product was purified by chromatography (silica gel eluted with 40% ethyl acetate in hexane). The purified product (4.7 g, 83%) was obtained as a solid which after recrystallization from a mixture of diethyl ether and hexane had m.p. 115.5°–117.5° C.

IR (film, AgCl) 3453, 2943, 1732, 1438, 1373, 1246 cm$^{-}$.

$^1$H NMR (CDCl$_3$) δ 4.58 (t, 1H, J=8.5 Hz, CHOAc), 3.73 (m, 1H of CH$_2$OH), 3.68 (s, 3H, COOCH$_3$), 3.63 (m, 1H of CH$_2$OH), 2.56 (dd, J=14.4 Hz, 2.4 Hz, 1H of CH$_2$COOCH$_3$), 2.04 (s, 3H, OCOCH$_3$), 0.77 (s, 6H, CH$_3$ (C$_{3a}$) and CH$_3$ (C$_6$)).

Elemental Analysis: For C$_{22}$H$_{36}$O$_5$. Calcd: C, 69.44; H, 9.54. Found: C, 69.23; H, 9.52.

Structure:

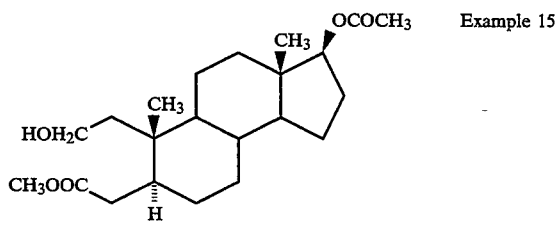

Example 15

EXAMPLE 16

Preparation of Methyl [3S-(3α,3aα,5aβ,6β,7α,9aα,9bβ)]-3-Acetyloxy)-6-[2E-(acetyloxy)ethenyl]-dodecahydro-3a,6-dimethyl-1H-benz[e]-indene-7-acetic acid and Methyl [3S-(3α,3aα,5aβ,6β,7α,9aα,9bβ)]-3-(Acetyloxy)-6-[2Z-(acetyloxy)ethenyl]-dodecahydro-3a,6-dimethyl-1H-benz[e]indene-7-acetic acid A solution of the compound of Example 15 (4.7 g, 12.3 mmol) in dichloromethane (50 mL) was added rapidly to a suspension of pyridinium chloroformate (10.81 g, 50.15 mmol) in dichloromethane and stirred at room temperature under nitrogen. After 3 h, the volume of dichloromethane was reduced to 40 mL on a rotary evaporator and then poured into diethyl ether (750 mL). The ether was passed through a small column of Florisil and additional diethyl ether was used to wash the Florisil and elute the steroid. The diethyl ether was removed on a rotary evaporator and the crude aldehyde product (4.6 g) immediately combined with isopropenyl acetate (60 mL) and p-toluenesulfonic acid (0.5 g) and refluxed for 16 h. The solution was then gently distilled for 1 h until about 10 mL of distillate was collected and then cooled to room temperature. The solution was poured into dichloromethane and washed with water (50 mL), 5% aq. NaHCO$_3$, and water (3×100 mL). The organic layer was dried over MgSO$_4$, filtered, and removed on a rotary evaporator to give slightly yellow crystals (5.6 g), which were purified by chromatography (silica gel eluted with 4% ethyl acetate in dichloromethane) to give 3.7 g of product. Recrystallization from a mixture of ethyl acetate and hexane gave 1.83 g (36%) of a mixture of the E and Z enol acetates. The enol acetate isomers were separated by high performance liquid chromatography (Econosil 5 micron, 250 mm×4.6 mm, eluted at 2.0 mL/min with 10% ethyl acetate in hexane).

The major 6-[2E-(acetyloxy)ethenyl] isomer had m.p. 191°–192° C.

IR (film, AgCl): 2918, 1756, 1733, 1666, 1451, 1373, 1227 cm$^{-1}$.

$^1$H NMR (CDCl$_3$): δ 6.98 (d, J=12.7 Hz, 1H, AcOCH=CH), 5.15 (d, J=12.7 Hz, 1H, AcOCH=CH), 4.56 (t, J=8.5 Hz, 1H, CHOAc), 3.63 (s, 3H, COOCH$_3$), 2.41 (dd, J=15.2 Hz, J=2.8 Hz, 1H of CH$_2$COOCH$_3$), 2.03 (s, 3H, OCOCH$_3$), 2.11 (s, 3H, OCOCH$_3$), 0.87 (s, 3H, CH$_3$ (C$_6$)), 0.76 (s, 3H, CH$_3$ (C$_{3a}$)).

Elemental Analysis: For C$_{24}$H$_{36}$O$_6$. Calcd: C, 68.55; H, 8.63. Found: C, 68.75; H, 8.70.

Structure:

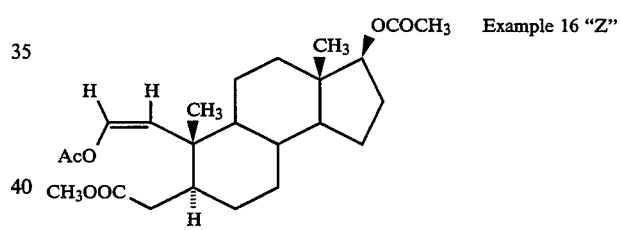

Example 16 "Z"

The minor 6-[2Z-(acetyloxy)ethenyl] isomer had m.p. 109.5°–112° C.

IR (film, AgCl): 2936, 1759, 1735, 1668, 1437, 1371, 1246, 1217 cm$^{-1}$.

$^1$H NMR (CDCl$_3$): δ 6.70 (d, J=7.6 Hz, 1H, AcOCH=CH), 4.58 (t, J=8.5 Hz, 1H, CHOAc), 4.39 (d, J=7.5 Hz, 1H, AcOCH=CH), 3.64 (s, 3H, COOCH$_3$), 2.44 (d, J=14.3 Hz,, 1H of CH$_2$COOCH$_3$) 2.11 (s, 3H, OCOCH$_3$), 2.03 (s, 3H, OCOCH$_3$), 1.06 (s, 3H, CH$_3$ (C$_6$)), 0.79 (s, 3H, CH$_3$ (C$_{3a}$)).

Elemental Analysis: For C$_{24}$H$_{36}$O$_6$. Calcd: C, 68.55; H, 8.63. Found: C, 68.93; H, 8.73.

Structure:

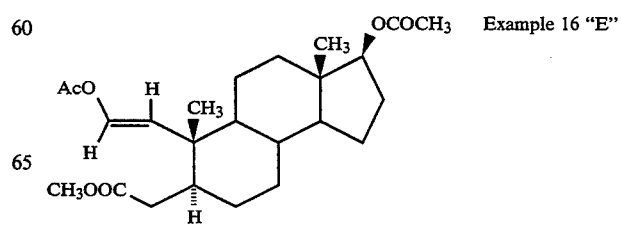

Example 16 "E"

EXAMPLE 17

Preparation of Methyl [3S-(3α,3aα,5aβ,6α,7α,9aα,9bβ)]-3-(Acetyloxy)-dodecahydro-3a,6-dimethyl-1H-benz[e]indene-7-acetic acid A solution of a mixture of the enol acetates of Example 16 (200 mg, 0.48 mmol) in dichloromethane (25 mL) and acetic acid (0.5 mL) was cooled to −78° C. in an acetone-dry ice bath and treated with $O_3$ until a blue color persisted. The excess $O_3$ was removed by bubbling the solution with $O_3$. After adding methyl sulfide (1 drop), dichloromethane (75 mL) was added and the solution was washed with water, 5% aq. $NaHCO_3$, and water again. The dichloromethane was dried over $MgSO_4$, filtered, and removed on a rotary evaporator to yield a yellow oil (158 mg). The oil was combined with Wilkinson's catalyst (3×500 mg added in equal portions, initially and after 72 and 120 h) in benzonitrile (25 mL) and heated to 150°–180° C. for 144 h under nitrogen. After cooling, ethyl acetate (50 mL) was added and the mixture was filtered. Removal of the solvents from the filtrate yielded a brown sludge (2.0 g) which was chromatographed (silica gel eluted with hexane/ethyl acetate mixtures) to give 25.4 mg (17.5%) pure product as a white solid, m.p. 61°–63° C.

IR (film, AgCl): 2922, 1737, 1437, 1373, 1248 $cm^{-1}$.

$^1H$ NMR ($CDCl_3$): δ 4.61 (t, J=7.82 Hz, 1H, CHOAc), 3.67 (s, 3H, $COOCH_3$), 2.56 (s, 3H, $OCOCH_3$), 0.78 (s, 3H, $CH_3$), 0.77 (s, 3H, $CH_3$).

Elemental Analysis: For $C_{20}H_{32}O_4$. Calcd: C, 71.39; H, 9.59; Found: C, 70.96; H, 9.62.

Structure:

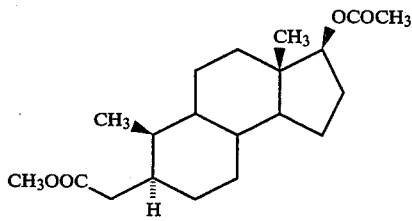

Example 17

EXAMPLE 18

Preparation of [3S-(3α,3aα,5aβ,6α,7α,9aα,9bβ)]-Dodecahydro-3a,6-dimethyl-1H-benz[e]indene-7-acetic acid To a solution of the compound of Example 17 (674 mg, 2.0 mmol) in methanol (50 mL) was added an aq. solution of NaOH (0.38 g in 5 mL water). After stirring at room temperature for 18 h, aq. HCl (6N, 20 mL) was added, and the reaction mixture was poured into water (10 mL). The product precipitated and was recovered as a white solid by filtration. It was recrystallized from aq. methanol to give 418 mg (74%) pure product as fine white crystals, m.p. 208°–210° C.

IR (film, NaCl): 3367, 2926, 1710, 1352, 1055, 1032 $cm^{-1}$.

$^1H$ NMR ($CDCl_3$): δ 3.62 (t, J=8.8 Hz, 1H, CHOH), 0.76 (d, J=6.1 Hz, 3H, $CH_3$ ($C_6$)), 0.71 (s, 3H, $CH_3$ ($C_{3a}$)).

Elemental Analysis: For $C_{17}H_{28}O_3$. Calcd: C, 72.82; H, 10.06; Found: C, 73.00; H, 10.18.

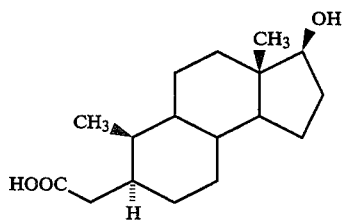

Example 18

EXAMPLE 19

Hippocampal Cell culture Methods

Under halothane anesthesia, 1 day old albino rat pups are sacrificed by rapid decapitation and the hippocampi are dissected and dissociated with papain (1 mg/ml in oxygenated L-15 media for 30 min at 35° C.) and mechanical trituration (18). Cells are plated on collagen coated-culture dishes at a density of 300,000 cells/ml. The growth media consists of Eagles Minimal Essential Media (MEM) supplemented with 5% fetal calf serum, 5% horse serum, 17 mM glucose, 0.4 mM glutamine, 50 U/ml penicillin and 50 μg/ml streptomycin. After three days in culture cells are treated with 10 μM cytosine arabinoside (ARA-C) to suppress glial growth. Cells are subsequently fed with fresh media once per week.

Electrophysiological methods

For recording purposes the growth media is replaced with a solution containing (in mM): 140 NaCl, 5 KCl, 2 $CaCl_2$, 1 $MgCl_2$, 10 glucose, 10 HEPES, 0.001 tetrodotoxin, pH=7.3. Neurons are studied using patch clamp recording techniques (12) with pipettes containing (in mM): 145 CsCl, 5 BAPTA, 5 NaCl, 0.5 $CaCl_2$, 2 MgATP, 10 HEPES, pH=7.3. This CsCl intracellular solution sets the Cl⁻ equilibrium potential ($E_{cl}$) at 0 mV (i.e. symmetric transmembrane concentrations of Cl⁻). This allows reliable recording of Cl⁻ currents without concern for shifts in transmembrane Cl⁻ concentration which can alter GABA responses during longer agonist exposures (1). In some tests examining effects on GABA IV curves, $E_{cl}$ is manipulated by replacing CsCl with $CsMeSO_4$. This shifts $E_{cl}$ to −81 mV. By comparing changes in IV curves in the two intracellular solutions greater confidence is had that responses are mediated by Cl⁻-selective ion channels. BAPTA and MgATP are included in the recording pipette to prevent problems with response rundown which sometimes occurs in whole-cell recording (44). The tests are conducted at room temperature (22° C.).

Table 1, below, sets forth the results obtained in the potentiation of GABA currents with the four illustrative preferred tricyclic steroid compounds compared to the control compound, 3α-OH-DHP.

TABLE 1

Potentiation of GABA Currents by Tricyclic Analogs

| Compound | Concentrations Tested | | Concentration for Direct |
|---|---|---|---|
| | 0.1 μM (N) | 1.0 μM (N) | Cl⁻ Current Activation |
| [structure: 3α-hydroxy-5β-pregnan-20-one type steroid] | 110 ± 5(3) | 195 ± 16(9) | >1 μM |
| [tricyclic structure with R substituent] R = =O | 95 ± 3(6) | 127 ± 5(6) | * |
| CN | 176 ± 9(8) | 346 ± 2(6) | * |
| NH–◁ | 237 ± 18(7) | 433 ± 20(8) | * |
| COCH₃ | 297 ± 7(11) | 489 ± 19(12) | * |

*No response up to 10 μM.
Values represent mean ± SEM; results are expressed as percent of control response to 1 μM GABA.

Various other examples will be apparent to the person skilled in the art after reading the present disclosure without departing from the spirit and scope of the invention. It is intended that all such other examples be included within the scope of the appended claims.

LITERATURE CITED

1. Akaike N, Inomata N, Tokutomi N (1987). Contribution of chloride shifts to the fade of γ-aminobutyric acid-gated currents in frog dorsal root ganglion cells. *J. Phyisol. (London)* 391, 219–234.
2. Baker K, Yang J, Covey DF, Clifford DB, Zorumski CF (1988). Alpha substituted thiobutyrolactones potentiate GABA currents in voltage clamped chick spinal cord neurons. *Neurosci. Lett.*, 87, 133–138.
3. Barker JL, Harrison NL, Lange GD, Owen DG (1987). Potentiation of gammaaminobutyric-acid-activated chloride conductance by a steroid anaesthetic in cultured rat spinal neurones. *J. Physiol.(London)*, 386, 485–501.
4. Baulieu EE, Robel P (1990). Neurosteroids: a new brain function? *J. Steroid Biochem. Molec. Biol.*, 37, 395–403.
5. Borman J (1988). Electrophysiology of GABA$_A$ and GABA$_B$ receptor subtypes. *Trends Neurosci.*, 11, 112–116.
6. Callachan H, Cottrell GA, Hather NY, Lambert JJ, Nooney JM, Peters JA (1987). Modulation of the GABA$_A$ receptor by progesterone metabolites. *Proc. R. Soc. Lond. B*, 231, 359–369.
7. Choi DW, Farb DH, Fischback GD (1981). Chlordiazepoxide selectively potentiates GABA conductance of spinal cord and sensory neurons in cell culture. *J. Neurophysiol*, 45, 621–631.
8. Crawley JN, Glowa JR, Majewska MD, Paul SM (1986). Anxiolytic activity of an endogenous adrenal steroid. *Brain Research*, 398, 382–385.
9. Dryden, Jr. HL (1972). Reductions of steroids by metal-ammonia solutions. In: *Organic Reactions in Steroid Chemistry*. (Eds. Fried J and Edwards JA) Van Nostrand Reinhold, New York, pp. 1–60.
10. Gee KW (1988). Steroid modulation of the GABA/benzodiazepine receptor-linked chloride ionophore. *Mol. Neurobiol.*, 2, 291–317.
11. Gee KW, Bolger MB, Brinton RE, Coirini, McEwen BS (1988). Steroid modulation of the chloride ionophore in rat brain: structure-activity requirements, regional dependence and mechanism of action. *J. Pharmacol. Exp. Ther.*, 246, 803–812.
12. Hamill OP, Marty A, Neher E, Sakmann B, Sakmann FJ (1981). Improved patch-clamp techniques for high resolution current recordings from cells and cell-free membrane patches. *Pfluegers Arch*, 391, 85–100.
13. Harrison NL, Majewska MD, Harrington JW, Barker JL (1987). Structure-activity relationships for steroid interaction with the gamma-aminobutyric acid$_A$ receptor complex. *J. Pharmacol. Exp. Ther.*, 241, 346–353.
14. Harrison NL, Vicini S, Barker JL (1987). A steroid anesthetic prolongs inhibitory postsynaptic currents in cultured rat hippocampal neurons. *J. Neurosci.*, 7, 604–609.
15. Harrison NL, Majewska MD, Meyers DER, Barker JL (1989). Rapid actions of steroids on CNS neurons. In: *Neural Control of Reproductive Function*. Alan Liss, New York, pp. 137–166.
16. Holland KD, Ferrendelli JA, Covey DF, Rothman SM (1990). Physiological regulation of the picrotoxin receptor by γ-butyrolactones in cultured hippocampal neurons. *J. Neurosci*, 10, 1719–1727.
17. Holland KD, Yoon KW, Ferrendelli JA, Covey DF, Rothman SM (1991). γ-Butyrolactone antagonism of the picrotoxin receptor: comparison of a pure antagonist and a mixed antagonist/inverse agonist. *Mol. Pharmacol.* 39, 79–84.
18. Huettner JE, Baughman RW (1986). Primary culture of identified neurons from the visual cortex of postnatal rats. *J. Neurosci*, 8, 160–175.
19. In WB, Blakeman DP, Davis JP, Ayer DE (1990). Studies on the mechanism of interactions between anesthetic steroids and γ-aminobutyric acid$_A$ receptors. *Mol. Pharmacol*, 37, 429–434.
20. Kavaliers M (1988). Inhibitory influences of the adrenal steroid, 3α,5α-tetrahydroxycorticosterone on aggression and defeat-induced analgesia in mice. *Psychopharmacology*, 95, 488–492.
21. Majewska MD (1988). Interaction of ethanol with the GABA$_A$ receptor in the rat brain: possible involvement of endogeneous steroids. *Alcohol*, 5, 269–273.
22. Majewska MD, Mienville J-M, Vicini S (1988). Neurosteroid pregnenolone sulfate antagonizes electrophysiological responses to GABA in neurones. *Neuroscience Lett.*, 90, 279–284.
23. Majewska MD, Demirgoren S, Spivak CE, London ED (1990). The neurosteroid dehydroepiandrosterone sulfate is an allosteric antagonist of the GABA$_A$ receptor. *Brain Research*, 526, 143–146.
24. Majewska MD, Harrison NL, Schwartz RD, Barker JL, Paul SM (1986). Steroid hormone metabolites are barbiturate-like modulators of the GABA receptor. *Science*, 232, 1004–1007.
25. Majewska MD (1987). Steroids and brain activity. *Biochem. Pharmacol.*, 22, 3781–3788.
26. Mendelson WB, Martin JV, Perlis M, Wagner R, Majewska MD, Paul SM (1987). Sleep induction by an adrenal steroid in the rat. *Psychopharmacology*, 93, 226–229.
27. Mienville JM, Vicini S (1989). Pregnenolone sulfate antagonizes GABA$_A$ receptor-mediated currents via a reduction of channel opening frequency. *Brain Res.* 489, 190–194.
28. Morgan M, Whitman JG (1985). Althesin. *Anesthesia*, 40, 121–123.
29. Morrow AL, Pace JR, Purdy RH, Paul SM (1990). Characterization of steroid interactions with gamma-aminobutyric acid receptor-gated chloride ion channels: evidence for multiple steroid recognition sites. *Mol. Pharmacol.*, 37, 263–270.
30. Murphy BEP. (1991). Steroids and depression. *J. Steroid Biochem. Molec. Biol.* 38, 537–559.
31. Ong, J, Kerr DIB., Johnston GAR. (1987). Cortisol: a potent biphasic modulator at GABA$_A$-receptor complexes in the guinea pig isolated ileum. *Neurosci. Lett.* 82, 101–106.
32. Peters JA, Kirkness EF, Callahan H, Lambert JJ, Turner AJ (1988). Modulation of the GABA$_A$ receptor by depressant barbiturates and pregnane steroids. *Br. J. Pharmacol.*, 94, 1257–1269.
33. Peterson SL (1989). Anticonvulsant profile of an anesthetic steroid. *Neuropharmacology*, 28, 877–879.
34. Phillipps GH (1974). Structure-activity relationships in steroidal anesthetics. In: *Molecular Mechanisms In General Anaesthesia*. (Eds. Halsey MJ, Millar R A, Sutton JA), Churchill Livingstone, New York, pp. 32–46.
35. Puia G, Santi M-R, Vicini S, Pritchett DB, Purdy RH, Paul SM, Seeburg PH, Costa E (1990). Neurosteroids act on recombinant human GABA$_A$ receptors. *Neuron*, 4, 759–765.
36. Purdy RH, Morrow AL, Moore, Jr PH, Paul SM (1991). Stress-induced elevations of gamma-aminobutyric acid type A receptor-active steroids in the rat brain. *Proc. Natl. Acad. Sci. USA*, 88, 4553–4557.
37. Purdy RH, Morrow AL, Blinn JR, Paul SM (1990). Synthesis, metabolism, and pharmacological activity of 3α-hydroxy steroids which potentiate GABA-receptor-mediated chloride ion uptake in rat cerebral cortical synaptoneurosomes. *J. Med. Chem.*, 33, 1572–1581.
38. Rosciszewska D, Buntner B, Guz I, Zawisza L (1986). Ovarian hormones, anticonvulsant drugs, and seizures during the menstrual cycle in women with epilepsy. *J. Neurol. Neurosurg. Psych.*, 49, 47–51.
39. Scholfield CN (1980). Potentiation of inhibition by general anesthetics in neurons of the olfactory cortex. *Pflugers Arch.* 383, 249–255.
40. Schulz DW, MacDonald RL (1981). Barbiturate enhancement of GABA-mediated inhibition and activation of chloride ion conductance: correlation with anticonvulsant and anesthetic actions. *Br. Res.* 209, 177–188.
41. Segal M, Barker JL (1984). Rat hippocampal neurons in culture; voltage clamp analysis of inhibitory connections. *J. Neurophysiol.* 52, 469–487.
42. Selye H (1941). Anesthetic effect of steroid hormones. *Proc. Soc. Exp. Biol. Med.*, 46, 116–121.
43. Sharpless KB, Lauer RF, Teranishi AY (1973). Electrophilic and nucleophilic organoselenium reagents. New routes to α,β-unsaturated carbonyl compounds. *J. Amer. Chem. Soc.*, 95,6137–6139.
44. Stelzer A, Kay AR, Wong RKS (1988). GABA$_A$ receptor function in hippocampal cells is maintained by phosphorylation factors. *Science* 241, 339–341.
45. Study RE, Barker JL (1981). Diazepam and (-)pentobarbital: fluctuation analysis reveals different mechanisms for potentiation of GABA responses in cultured central neurons. *Proc. Natl. Acad. Sci. (USA)* 78, 7180–7184.
46. Tsuji N, Suzuki J, Shiota M, Takahashi I, Nishimura S (1980). Highly stereoselective hydrogenation of 3-oxo-4-ene and -1,4-diene steroids to 5β compounds with palladium catalyst. *J. Org. Chem.*, 45, 2729–2731.
47. Turner DM, Ransom RW, Yang JS-J, Olsen R (1989). Steroid anesthetics and naturally occurring analogs modulate the gamma-Aminobutyric acid receptor complex at a site distinct from barbiturates. *J. Pharmacol. Exp. Ther.*, 248, 960–966.
48. Zorumski CF, Yang J, Baker K, Covey DF, Clifford DB, (1989). Convulsant gamma-butyrolactones block GABA currents in cultured chick spinal cord neurons. *Brain Res.* 484, 102–110.
49. Zorumski CF, Isenberg KE (1991). Insights into the structure and function of GABA-benzodiazepine receptors: ion channels and psychiatry. *Am. J. Psych.*, 148, 162–173.

What is claimed is:

1. The method of enhancing GABA-induced chloride currents at the GABA receptor/chloride ionophore complex comprising administering to a warm blooded mammal an effective amount of a compound of the following structural formula:

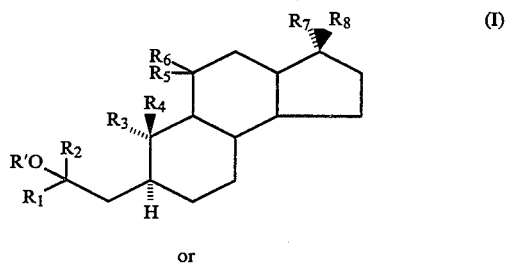

or

-continued

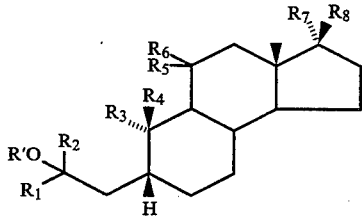 (II)

wherein
- $R_1$=H or $C_1$-$C_4$ alkyl or fluoroalkyl;
- $R_2$=H or $C_1$-$C_4$ alkyl or fluoroalkyl, in which $R_1$ and $R_2$ can be the same or different;
- $R_3$=H or $CH_3$;
- $R_4$=H or $CH_3$, in which $R_3$ and $R_4$ can be the same or different;
- $R_5$=H;
- $R_6$=H;
- $R_5,R_6$==O(carbonyl);
- $R_7$=H;
- $R_8$=a hydrogen bond accepting group;
- $R_7,R_8$==O(carbonyl); and
- R'=H or an ester group.

2. The method of claim 1 in which the administered compound has the structure

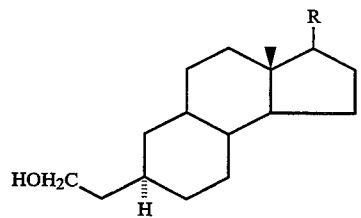

wherein R is ==O, CN,

or $COCH_3$.

3. The method of claim 2 in which R is ==O.
4. The method of claim 2 in which R is CN.
5. The method of claim 2 in which R is

.

6. The method of claim 2 in which R is $COCH_3$.

* * * * *